United States Patent
Toyohara et al.

(10) Patent No.: US 7,118,731 B2
(45) Date of Patent: Oct. 10, 2006

(54) DRUGS FOR THE DIAGNOSIS OF TISSUE REPRODUCTIVE ACTIVITY OR THE TREATMENT OF PROLIFERATIVE DISEASES

(75) Inventors: Jun Toyohara, Sodegaura (JP); Akio Hayashi, Sodegaura (JP)

(73) Assignee: Nihon Medi-Physics Co., Ltd., Hyogo (JP)

( * ) Notice: Subject to any disclaimer, the term of this patent is extended or adjusted under 35 U.S.C. 154(b) by 0 days.

(21) Appl. No.: 10/988,657

(22) Filed: Nov. 16, 2004

(65) Prior Publication Data

US 2005/0129611 A1      Jun. 16, 2005

Related U.S. Application Data

(62) Division of application No. 10/239,355, filed as application No. PCT/JP02/00408 on Jan. 22, 2002, now Pat. No. 7,045,115.

(51) Int. Cl.
*A61K 49/00* (2006.01)
(52) U.S. Cl. .............. 424/9.1; 424/1.11; 424/1.65; 424/1.85; 424/1.89; 424/1.73; 549/6
(58) Field of Classification Search ............... 424/1.11, 424/1.41, 1.65, 1.73, 1.81, 1.85, 1.89, 9.1, 424/9.2; 544/224; 548/400; 549/1, 200, 549/6
See application file for complete search history.

(56) References Cited

U.S. PATENT DOCUMENTS

| 5,077,034 A | 12/1991 | Kassis et al. |
| 5,422,345 A | 6/1995 | Dougan |
| 5,703,056 A | 12/1997 | Blasberg et al. |
| 5,720,935 A | 2/1998 | Kassis et al. |

FOREIGN PATENT DOCUMENTS

| EP | 0 421 777 A1 | 4/1991 |
| WO | WO 96/12508 | 5/1996 |
| WO | WO 96/23806 | 8/1996 |
| WO | WO 96/28190 | 9/1996 |
| WO | WO 96/41648 | 12/1996 |
| WO | WO 96/44646 | 9/1999 |
| WO | WO 01/054439 A1 | 1/2001 |

OTHER PUBLICATIONS

Vaidyanathan et al., "Preparation of 5-[$^{131}$I]Iodo- and 5-[$^{211}$At] Astato-1-(2-Deoxy-2-Fluoro-β-D-Arabinofuranosyl) Uracil by a Halodestannylation Reaction," Nuclear Medicine & Biology, vol. 25, p. 487-496, 1998.
Machida et al., "Anti-herpesvirus Activity Profile of 4'-thioarabinofuranosyl Purine and Uracil Nucleosides and Activity of 1-β-D-2'-thioarabinofuranosyl Guanine And 2,6-diaminopurine Against Clinical Isolates of Human Cytomegalovirus," Antiviral Research 39 (1998), pp. 129-137.
O'Donoghue, "Strategies for Selective Targeting of Auger Electron Emitters to Tumor Cells," The Journal of Nuclear Medicine, vol. 37, No. 4, Apr. 1996, pp. 3S-6S.
Bergström et al., "Synthesis of [$^{76}$Br] Bromofluorodeoxyuridine and Its Validation With Regard to Uptake, DNA Incorporation, and Excretion Modulation in Rats," The Journal of Nuclear Medicine, vol. 41, No. 10, Oct. 2000, pp. 1746-1752.
Ganesan Vaidyanathan et al., Preparation of 5-[$^{131}$I]Iodo- and 5-[$^{211}$At]Astato-1-(2-Deoxy-2-Fluoro-β-D-Arabinofuranosyl) Uracil by a Halodestannylation Reaction, Nuclear Medicine & Biology, vol. 25, pp. 487-496, 1998.

Primary Examiner—Dameron L. Jones
(74) Attorney, Agent, or Firm—Fitch, Even, Tabin & Flannery

(57) ABSTRACT

An agent which comprises, as an active ingredient, a radiolabeled compound as represented by the following formula or a pharmaceutically acceptable salt thereof:

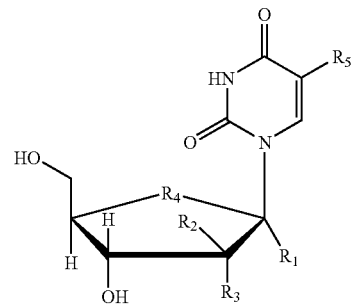

wherein $R_1$ denotes hydrogen, or a linear- or branched-chain alkyl group having 1–8 carbon atoms, $R_2$ denotes hydrogen, hydroxyl or a halogen substituent, $R_3$ denotes hydrogen or fluorine substituent, $R_4$ denotes oxygen, sulfur, or a methylene substituent, and $R_5$ denotes a radioactive halogen substituent.

The agent is stable in vivo, and either stays in cells or is incorporated in DNA, thus serving for diagnosis of tissue proliferation activity or treatment of proliferative disease.

9 Claims, 11 Drawing Sheets

DRUGS FOR THE DIAGNOSIS OF TISSUE REPRODUCTIVE ACTIVITY OR THE TREATMENT OF PROLIFERATIVE DISEASES

CROSS-REFERENCED APPLICATIONS:

This application is divisional application of U.S. application Ser. No. 10/239,355, filed Sep. 23, 2002 now U.S. Pat. No. 7,045,115, the complete disclosure of which is incorporated herein by reference, which was the National phase of International Application PCT/JP02/00408, filed 22 Jan. 2002, which designated the U.S. and that International Application was not published under PCT Article 21(2) in English.

TECHNICAL FIELD

The present invention relates to use of radiolabeled nucleoside derivatives for diagnosis of tissue proliferation activity and treatment of proliferative diseases.

BACKGROUND ART

If proliferation activity of tumor cells can be determined non-invasively by image diagnosis, it will be help for evaluation of growth rate and malignancy of the tumor. Detection of the most rapidly growing regions of a tumor by image diagnosis will be useful in preparing plans for radiation fields in radiotherapy and identifying suitable portions for biopsy. Such methods will permit an early and accurate evaluation of therapeutic effects, which is difficult to identify by CT- or MRI-based anatomical evaluation or PET-based measurement of glucose-metabolic changes. Particularly, they will be useful for an early assessment of therapeutic effects of anticancer agents that may cause strong side effects.

In order to solve these clinically important problems, use of 5-iodo-deoxyuridine labeled with a radioactive iodine and thymidine labeled with carbon-11 which is a positron-emitter, have been studied (Tjuvajev J G et al., J. Nucl. Med. 35, pp.1407–1417 (1994); Blasberg R G et al, Cancer Res. 60, pp.624–635 (2000); Martiat Ph et al., J. Nucl. Med. 29, pp.1633–1637 (1998); Eary J F et al., Cancer Res. 59, pp. 615–621 (1999); U.S. Pat. Nos. 5,094,835; 5,308,605). It is considered that these radiolabeled compounds are taken into cells as precursors for DNA synthesis required for cell division of rapidly-growing tumors, and then phosphorylated by thymidine kinase, followed by incorporation into DNA, to reflect proliferation activity of the tumor. These radiolabeled compounds, however, are decomposed rapidly in vivo, making it difficult to perform non-invasive evaluation of the proliferation activity of the tumor. The method using carbon-11-labeled thymidine, in particular, requires very complicated mathematical model analysis, and cannot become popular as a diagnostic technique of nuclear medicine imaging.

The rapid metabolic decomposition of these radiolabeled compounds in vivo is considered to be due to cleavage of C—N glycosidic bonds by thymidine phosphorylase and instability of the labels in vivo. If the C—N glycosidic bonds are cleaved, the compound loses its affinity to tumors, thereby decreasing in accumulation of radioactivity in tumors, while the radioactive metabolites increase background radioactivity, thereby making imaging of the tumors difficult.

To solve these problems, radiolabeled compounds with metabolic stability have been synthesized by introducing fluorine atoms, which are high in electronegativity, to the 2' or 3' position in certain nucleosides, and have been studied for imaging of tumors. Thus, 3'-deoxy-3'-fluorothymidine that contains fluorine 18, a positron emitter, at the 3' position shows a high stability in vivo and an accumulation in tumor tissue (Shields A F et al., Nature Med. 4, pp.1334–1336 (1998)). Though this radiolabeled compound is stable in vivo, it is a radio-labeled compound with a short-life positron emitter, and therefore a cyclotron is required in the hospital, limiting the usage of the compound. For this radiolabeled compound, the major process responsible for its accumulation in cells is the phosphorylation caused by thymidine kinase that is an index of DNA synthesis, and thus it does not serve as an agent that essentially reflects DNA synthesis.

A derivative of 5-iododeoxyuridine, in which fluorine is introduced to the 3' position in the same manner as above to increase its stability in vivo, has recently been reported. Though stable in vivo, however, this radiolabeled compound was high in retention in blood and failed to show a significant accumulation in a tumor compared to 5-iododeoxyuridine (Choi S R et al., J. Nucl. Med. 41, p. 233 (2000)).

2'-fluoro-5-iodoarabinouridine, in which fluorine is introduced to the 2' position, shows a high stability in vivo, and has been used for identification of introduction and expression in vivo of a vector for gene therapy, utilizing a phosphorylation reaction specific to thymidine kinase of human herpesvirus. It has also been applied to image diagnosis for virus infection, based on the high specificity to the viral thymidine kinase (Tjuvajev J G et al., Cancer Res. 56, pp.4087–95 (1996); Tjuvajev J G et al., Cancer Res. 58, pp.4333–4441 (1998); Wiebe L I et al., Nucleosides Nucleotides 18, 1065–1076 (1999); Gambhir S S et al., Nucl. Med. Biol. 26, pp.481–490 (1999); Haubner R et al., Eur. J. Nucl. Med. 27, pp.283–291 (2000); Tjuvajev J G et al. Cancer Res. 59, 5186–193 (1999); Bengel F M et al., Circulation 102, pp.948–950 (2000)).

In view of the above situation, the present invention aims to provide a radiolabeled compounds that are practically useful in clinical fields, stable in vivo, and able to retain in cells after being phosphorylated by thymidine kinase of mammals, or reflect the DNA synthesis activity after being incorporated in DNA, particularly those compounds which are labeled with a single-photon emitter to achieve a wide spectrum of use, and also aims to provide methods for diagnosis of tissue proliferation activity and for treatment of proliferative disease, utilizing agents that contain said radiolabeled compounds.

DISCLOSURE OF THE INVENTION

To achieve the above-mentioned objectives, the present inventors have synthesized a variety of radiolabeled compounds and have intensively studied to see if they are useful for image evaluation of tissue proliferation activity. As a result, the inventors have found that radiolabeled compounds as represented by the following formula can serve for diagnosis of tissue proliferation activity or treatment of proliferative disease, and have completed the present invention.

Specifically, the present invention provides an agent for diagnosis of tissue proliferation activity or for treatment of proliferative disease, which comprises, as an active ingredient, a radiolabeled compound as represented by the following formula or a pharmaceutically acceptable salt thereof:

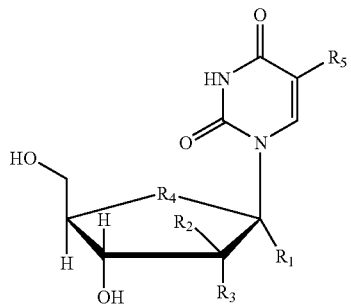

wherein $R_1$ denotes hydrogen, or a linear- or branched-chain alkyl group having 1–8 carbon atoms; $R_2$ denotes hydrogen, hydroxyl, or a halogen substituent; $R_3$ denotes hydrogen or fluorine substituent, $R_4$ denotes oxygen, sulfur or a methylene substituent, and $R_5$ denotes a radioactive halogen substituent, excluding the case where $R_1$, $R_2$ and $R_3$ are hydrogen, $R_4$ being oxygen, and $R_5$ being radioactive fluorine, bromine, iodine, or astatine; the case where $R_1$ and $R_3$ are hydrogen, $R_2$ being fluorine, $R_4$ being oxygen, and $R_5$ being radioactive bromine or iodine; and the case where $R_1$ and $R_2$ are hydrogen, $R_3$ being fluorine, $R_4$ being oxygen, and $R_5$ being radioactive bromine or iodine.

The radiolabeled compounds of the present invention are stable in vivo, and can retain in cells after being phosphorylated by mammalian thymidine kinase or reflect the DNA synthesis activity after being incorporated in DNA. Therefore, they realize effective diagnosis of tissue proliferation activity and treatment of proliferative disease, and are particularly useful as diagnostic radioactive imaging agents for diagnosis of tissue proliferation activity or as radioactive therapeutic agents for treatment of proliferative disease in accordance with internal radiotherapy, local radiotherapy or the like.

Thus, according to another aspect of the present invention, there are provided methods for diagnosis of tissue proliferation activity, which comprise administering an effective amount of a radiolabeled compound as represented by the above formula or a pharmaceutically acceptable salt thereof to a mammal, followed by imaging in vivo distribution thereof, and methods for treatment of proliferative disease, which comprises administering an effective amount of said radiolabeled compound or salt to a mammal. Herein, mammal includes human beings.

In the present invention, the radiolabeled compounds as represented by the above formula include salts thereof, or may be in a form of a hydrate or solvate of these. Such salts include pharmaceutically acceptable salts, for example, one formed with a mineral acid such as hydrochloric acid and sulfuric acid or with an organic acid such as acetic acid. As such a hydrate or solvate, mention may be made of the present radiolabeled compounds or salts thereof to which water molecules or solvent molecules are attached. Furthermore, the compounds of the present invention include their various isomers such as tautomers.

In the above formula, the linear- or branched-chain alkyl group having 1–8 carbon atoms as represented by $R_1$ includes, for example, methyl group, ethyl group, propyl group, t-butyl group, and n-hexyl group, of which methyl group is preferable. The halogen-substituent as represented by $R_2$ preferably includes fluorine, chlorine, and bromine. $R_4$ is preferably oxygen or sulfur, of which sulfur is particularly preferable.

The radioactive halogen-substituent as represented by $R_5$ in the above formula includes F-18, Cl-36, Br-75, Br-76, Br-77, Br-82, I-123, I-124, I-125, I-131, and At-211, of which F-18, Br-76, I-123, and I-124 are preferable for diagnostic purposes while Br-77, I-125, I-131, and At-211 are preferable for therapeutic purposes.

Preferred compounds as represented by the above formula include those wherein $R_1$ is hydrogen or methyl, $R_2$ is hydrogen or a halogen-substituent, $R_3$ is hydrogen, and $R_4$ is oxygen or sulfur, particularly preferably those wherein $R_1$, $R_2$ and $R_3$ are hydrogen, $R_4$ is sulfur, $R_5$ is a radioactive halogen-substituent selected from F-18, I-123, I-125, and I-131.

Certain 4'-thio nucleic acid derivatives as represented by the above formula (where $R_5$ is a non-radioactive halogen-substituent) have been reported to be resistant to bacterial thymidine phosphorylase as a result of studies on antiviral agents (Dyson M R et al., J. Med. Chem. 34, pp.2782–2786 (1991); Rahim S G et al., J. Med. Chem. 39, pp.789–795 (1996)). It has also been known that certain 5-iodine- and 5-methyl-4'-sulfur substitution products inhibit phosphorylation of thymidine by human thymidine kinase (Strosselli S et al., Biochem J. 334, pp.15–22 (1998)). The chemical structures of these compounds with sulfur at the 4' position and their use as an antiviral agent are already known (International Publication WO9101326, International Publication WO9104982, Japanese Patent Laid-Open No. HEI 10-087687), but neither the corresponding radiolabeled compounds nor their use as a radioactive diagnostic imaging agent or radioactive therapeutic agent have been known.

The chemical structures of certain compounds with a substituent at the 1' position as represented by the above formula (where $R_5$ is a non-radioactive substituent) and production methods thereof have already been known (Japanese Patent Laid-Open No. HEI 07-109289). However, neither the corresponding radiolabeled compounds nor their use as a radioactive diagnostic imaging agent or radioactive therapeutic agent have been known.

The compounds as represented by the above formula can be used for various diagnoses of tissue proliferation activity and treatment for proliferative diseases by virtue of their in vivo stability and their capability for retention in cells or capability for being incorporated in DNA.

Such diagnoses of tissue proliferation activity include, for example, diagnosis of hyperplasia, regeneration, transplantation or viral infection accompanied by abnormal proliferation.

The diagnosis of hyperplasia accompanied by abnormal proliferation includes, for example, diagnosis of hyperplastic inflammation, benign tumors, or malignant tumors. The diagnosis of the hyperplastic inflammation includes, for example, diagnoses concerning activity of chronic rheumatoid arthritis and determination of therapeutic effects. The diagnosis of the benign tumors includes, for example, diagnoses concerning localization, activity and determination of therapeutic effects. The diagnosis of the malignant tumors includes, for example, diagnoses concerning localization, progress, malignancy and determination of therapeutic effects, of primary and metastatic malignant tumors. Benign tumors include, for example, prostatic hyperplasia, endometrium hyperplasia (cystic hyperplasia, adenomyosis uteri, hysteromyoma), ovarian tumor (cystadenoma), mammary gland (mastopathy, mammary gland fibroadenoma), pituitary adenoma, craniopharyngioma, thyroid adenoma, adrenocortical adenoma and pheochromocytoma. Malignant tumors include, for example, malignant lymnphoma (Hodgkin's disease, non-Hodgkin lymphoma), pharyngeal cancer, lung cancer, esophagus cancer, gastric cancer, colon cancer, hepatic cancer, pancreatic cancer, nephtic tumor (nephric cancer, nephroblastoma), bladder tumor, prostatic cancer, testicular tumor, uterine cancer, ovarian cancer, breast cancer, thyroid cancer, neuroblastoma, brain tumor (primary brain tumor, metastatic brain tumor), rhabdomyosarcoma, bone tumor (osteosarcoma, metastatic bone tumor), Kaposi's sarcoma, and malignant melanoma.

The diagnosis of regeneration accompanied by abnormal proliferation is exemplified by diagnosis of function of physiological regeneration of blood and diagnosis of pathological regeneration resulting from pathological loss of blood cells, such as evaluation of physiological hematopoietic functions of bone marrow during treatment with anticancer drugs and diagnosis of pathological functions of the bone marrow in patients suffering from hypoplastic anemia.

The diagnosis of transplantation accompanied by abnormal proliferation is exemplified by diagnosis of blood cancer patients undergoing bone marrow transplantation or very high-dose chemotherapy using an anticancer agent, such as diagnosis of take or proliferation of transplanted bone marrow cells in bone marrow transplantation.

The diagnosis of viral infection accompanied by abnormal proliferation includes, for example, diagnosis of virus-infected portions and proliferation thereof in infectious diseases caused by Type I or Type II herpes simplex virus, varicella-zoster herpes virus, cytomegalovirus, Epstein-Barr virus, or human immunodeficiency virus, particularly infectious diseases of central nervous system (e.g., viral-infectious cerebritis, meningitis, etc.) caused by Type I or Type II herpes simplex virus or human immunodeficiency virus.

The treatment for proliferative diseases is exemplified by treatment of malignant tumors or viral infection accompanied by abnormal proliferation. Such malignant tumors include, for example, malignant lymphoma (Hodgkin's disease, non-Hodgkin lymphoma), pharyngeal cancer, lung cancer, liver cancer, bladder tumor, rectal cancer, prostatic cancer, uterine cancer, ovarian cancer, breast cancer, brain tumor (primary brain tumor, metastatic brain tumor), and malignant melanoma. Such a viral infection includes infectious diseases of central nervous system caused by Type I or Type II herpes simplex virus or human immunodeficiency virus, particularly viral encephalitis or meningitis.

Methods for labeling the compounds represented by the above formula at the "5" position with a radioactive halogen may be known methods, such as methods using isotope exchange reaction, and a method using a 5-chloromercuri compound in which mercury is introduced into the "5" position of the compound or a 5-hydrogen compound in which there is no substitution at the "5" position of the compound. The method using the 5-chloromercuri compound is already known as an iodo-labeling method for producing 5-iodo-2'-deoxyuridine (U.S. Pat. No. 4,851,520; Baranowska-Kortylewicz J et al., Appl. Radiat. Isot. 39, p.335 (1988)). This method is, however, disadvantageous for producing pharmaceuticals labeled with a short half-time radioactive nuclide due to side reactions (formation of "5-chloro" compounds, demercurization reaction), a long reaction time (6 hours), and formation of inorganic mercury compounds. The method using a 5-hydrogen compound is already known as a method for producing 5-iodo-2'-deoxyuridine from 2'-deoxyuridine (Knaus E E et al., Appl. Radiat. Isot. 37, p.901 (1986); Fin R D et al., J. Label. Comds. Radiopharm. 40, p.103 (1997)). This method, however, requires heating at 65–115° C., and therefore, it is not suitable for use with compounds that are easily decomposed under heating conditions and cannot be said to be an ideal labeling method, considering the properties of radioactive halogen atoms which preferably should not involve heating operations during the labeling reaction. Further, the radiolabeling method using isotope exchange reaction is also unsuitable for producing pharmaceuticals that must be maintained at a certain level of quality, because the method is not able to produce carrier-free labeled compounds and is difficult to control variation of specific activity among different labeling runs.

Another useful method for labeling the compounds represented by the above formula at the "5" position with a radioactive halogen is to allow a compound (5-trialkyltin compound), in which the pyrimidine base is substituted by a trialkylstannyl group at the "5" position as represented by Formula 11 in FIG. 1, Formula 21 in FIG. 2, Formula 28 in FIG. 3, Formula 40 in FIG. 4, Formula 50 in FIG. 5 or Formula 58 in FIG. 6, to react with 0.1N sodium hydroxide solution of a radioactive halogen in an appropriate solvent such as chloroform, so that the trialkylstannyl group at the "5" position is converted into a radioactive halogen-substituent. This labeling method, which uses a 5-trialkyltin compound, is preferable as it does not suffer such problems as with the above three labeling methods. Specifically, this method requires only a relatively short reaction time, and it does not produce "5-chloro" compounds or need heating as the reaction readily proceeds at room temperature. The resulting labeled compounds are free of carriers, and if a lower specific activity is desired, a labeled compound with a fixed specific activity can be readily prepared by adding a carrier. This method is also featured in that purification after the reaction is easy to operate. Specifically, 5-trialkyltin compounds are largely different from the corresponding radioactive halogen-labeled compounds in terms of overall molecular polarity as the electrical properties at the "5" position differ between them. Owing to the difference in the molecular polarity, labeled compounds and unreacted precursors can be separated easily by using a commercial reverse-phase silica gel cartridge after the labeling reaction. This permits elimination of the need of troublesome high performance liquid chromatographic purification.

Thus, according to another aspect of the present invention, there is provided a method for producing a radiolabeled compound as represented by the following formula:

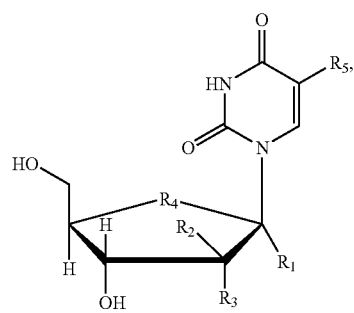

wherein $R_1$ denotes hydrogen or a linear- or branched-chain alkyl groups having 1–8 carbon atoms, $R_2$ denotes hydrogen, hydroxyl or a halogen substituent, $R_3$ denotes hydrogen or fluorine substituent, R₄ denotes oxygen, sulfur or a methylene substituent, and R₅ denotes a radioactive halogen substitient;

comprising reacting a nucleoside derivative as represented by the following formula:

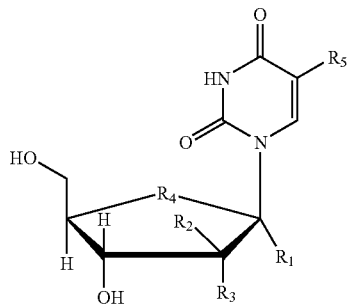

wherein R₁ denotes hydrogen or a linear- or branched-chain alkyl groups having 1–8 carbon atoms, R₂ denotes hydrogen, hydroxyl or a halogen substituent, R₃ denotes hydrogen or fluorine substituent, R₄ denotes oxygen, sulfur or a methylene substituent, and R₅ denotes a trialkylstannyl group, with an alkaline solution of a radioactive halogen in a solvent, whereby the trialkylstannyl group of R₅ is converted into the radioactive halogen substituent.

The 5-trialkyltin compounds as represented by Formula 11 in FIG. 1, Formula 21 in FIG. 2, Formula 28 in FIG. 3, Formula 40 in FIG. 4, Formula 50 in FIG. 5, and Formula 58 in FIG. 6 are novel compounds which are useful intermediates for producing the radiolabeled compounds of the present invention.

Thus, according to another aspect of the present invention, there is provided a compound as represented by the following formula:

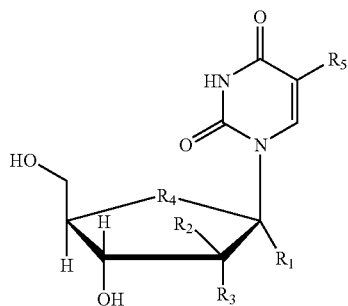

wherein R₁ denotes hydrogen or a linear- or branched-chain alkyl groups having 1–8 carbon atoms, R₂ denotes hydrogen, hydroxyl or a halogen substituent, R₃ denotes hydrogen or fluorine substituent, R₄ denotes oxygen, sulfur or a methylene substituent, and R₅ denotes a trialkylstannyl group.

In the above formula, the linear- or branched-chain alkyl groups having 1–8 carbon atoms as represented by R₁ include, for example, methyl group, ethyl group, propyl group, t-butyl group, and n-hexyl group, of which methyl group is preferred. The halogen-substituent as represented by R₂ preferably includes fluorine, chlorine and bromine. R₄ is preferably oxygen or sulfur. The trialkylstannyl group as represented by R₅ includes trimethylstannyl group, triethylstannyl group and tributylstannyl group.

Preferred compounds as represented by the above formula include those wherein R₁ is hydrogen or methyl, R₂ is hydrogen or a halogen-substituent, R₃ is hydrogen, and R₄ is oxygen or sulfur.

As seen from FIGS. 1–6, 5-trialkyltin compounds can generally be synthesized by providing their corresponding halogen-containing compound (as represented by Formula 10 in FIG. 1, Formula 20 in FIG. 2, Formula 27 in FIG. 3, Formula 39 in FIG. 4, Formula 49 in FIG. 5, or Formula 57 in FIG. 6) as starting materials, reacting the compound with bis(trialkyltin) and bis(triphenylphosphine)palladium chloride in anhydrous 1,4-dioxane under heat at reflux in an argon atmosphere, followed by purification.

Compound 10 (ITDU) in FIG. 1 can be synthesized by a known method (Formulae 1–8: Dyson, M R et al., Carbo. Res. 216, p.237 (1991), and Formulae 8–10: Oivanen, M et al., J. Chem. Soc., Perkin Trans. 2, p.2343 (1998)). Specifically, 2-deoxy-D-erythro-pentose (Compound 1) is reacted with a 1% hydrochloric acid-methanol solution to produce Compound 2, which is then reacted with sodium hydride, tetrabutylammonium iodide, and benzyl bromide to produce Compound 3, in which hydroxyl groups are protected. The compound is reacted with α-toluenethiol and concentrated hydrochloric acid to produce Compound 4, which is then reacted with triphenylphosphine, benzoic acid, and diethylazodicarboxylate to produce Compound 5. Sodium methoxide is then used to remove the benzoyl group from Compound 5 to produce Compound 6, followed by its conversion into Compound 7 with methanesulfonyl chloride. A ring is formed with sodium iodide and barium carbonate to produce Compound 8, which is reacted with 5-iodouracil in the presence of bistrimethylsilylacetamide and then with N-iodosuccinimide to produce Compound 9. Subsequently, Compound 9 is deprotected with titanic chloride to produce Compound 10.

Compound 20 (ITAU) in FIG. 2 can be synthesized by a known method (Formulae 13–17: Yoshimura Y et al., J. Org. Chem.61, p.822 (1996) and Formula 17–20: Yoshimura Y et al., J. Med. Chem. 40, p.2177 (1997)). Specifically, 1,2;5,6-di-O-isopropylidene glucose (Compound 13) is reacted with sodium hydride and benzyl bromide to produce a 3-benzyl compound, which is subsequently reacted with hydrochloric acid, aqueous sodium periodate solution, and sodium borohydride to produce Compound 14, which is then converted with hydrogen chloride into Compound 15. The compound is then reacted with mesyl chloride and sodium sulfide to produce Compound 16, which is reacted with hydrochloric acid and sodium borohydride successively to produce Compound 17. Hydroxyl groups are protected with sodium hydride and benzyl bromide (Compound 18), and the resulting compound is converted to Compound 19 with m-chloroperbenzoic acid (m-CPBA) and acetic anhydride. It is further reacted with 5-iodouracil in the presence of 1,1,1,3,3,3-hexamethylene disilazane (HMDS) to produce a glycosylated compound, which is then reacted with boron chloride to produce Compound 20.

Compound 27 in FIG. 3 can be produced as follows. Compound 17 shown in FIG. 2 is used as a starting material, which is reacted with t-butyldimethylsilyl chloride (TBDM-SCI) in dimethylformamide (DMF) in the presence of imidazole to protect the hydroxyl group at the "5" position with a silyl group to produce Compound 23. Trifluoromethanesulfonic acid anhydride (Tf₂O) is added thereto in pyridine to produce Compound 24 in which the hydroxyl group at the "2" position is trifluoromethanesulfonylated. The compound is reacted with potassium fluoride, along with Kryptofix (registered trademark) 222 and potassium carbonate, in acetonitrile, to produce a fluoride compound (Compound 25) in which the substituent at the "2" position is stereochemically reversed. The compound is reacted with m-chloroperbenzoic acid (m-CPBA) in methylene chloride and further treated with acetic anhydride to produce Compound 26. This is reacted with the product resulting from a reaction of 5-iodouracil and 1,1,1,3,3,3-hexamethylene disilazane (HMDS), and with trifluoromethanesulfonic acid trimethylsilyl (TMSOTf). The resulting product is further treated with boron chloride in methylene chloride to produce Compound 27.

Compound 39 (FIAU) in FIG. 4 can be synthesized by a known method (Formulae 30–37: Reichman U et al., Carbohydrate Res. 42, p.233 (1975) and Formulae 37–39: Asakura J et al., J. Org. Chem. 55, p.4928 (1990)). Specifically, Compound 31, which has been synthesized in four steps from 1,2:5,6-di-O-isopropylidene glucose (Compound 30), is treated with a cation exchange resin (Amberlite IR-120) to produce Compound 32, which is then reacted with potassium periodate to produce Compound 33. This is then reacted with sodium methoxide to produce Compound 34, followed by acetylation of hydroxyl groups to produce Compound 35. The compound is treated with a hydrogen bromide-acetic acid solution to produce Compound 36, followed by condensation with an uracil derivative to produce Compound 37. It is subsequently reacted with diammonium cerium(III) sulfate (CAN) to produce Compound 38, followed by deprotection of hydroxyl groups with sodium methoxide to produce Compound 39.

Compound 49 (FITAU) in FIG. 5 can be synthesized by a known method (Formulae 42–46: Yoshimura Y et al., J. Org. Chem. 62, p.3140 (1997) and Formulae 46–49: Yoshimura Y et al., Bioorg. Med. Chem. 8, p.1545 (2000)). Specifically, Compound 43, which has been synthesized in nine steps from 1,2:5,6-di-O-isopropylidene glucose (Compound 42), is reacted with diethylaminosulfur trifluoride (DAST) to produce Compound 44, which is then reacted with m-chloroperbenzoic acid (m-CPBA) to produce Compound 45. This is subsequently reacted with acetic anhydride to produce Compound 46, which is reacted with trifluoromethanesulfonic acid trimethylsilyl (TMSOTf) to cause condensation with a 5-iodouracil derivative to produce Compound 47. Finally, the two protective hydroxyl groups are removed to produce Compound 49.

Compound 57 (IMBAU) in FIG. 6 can be synthesized by a known method (Formulae 52–54: Itoh Y et al., J. Org. Chem. 60, p.656 (1995) and Formulae 55–56: Asakura J et al., J. Org. Chem. 55, p.4928 (1990)), combined with known reactions for protection and deprotection of hydroxyl groups (Formulae 54–55 and Formula 56–57). Specifically, 1-[3,5-bis-O-(tert-butyldimethylsilyl)-2-deoxy-D-erythro-pento-1-enofuranosyl]uracil (Compound 52) is reacted with pivalic acid and bromosuccinimide (NBS) to produce Compound 53, which is then reacted with trimethylaluminum to produce Compound 54. The protection groups for hydroxyl groups are converted from tert-butyldimethylsilyl to acetyl, followed by reaction with diammonium cerium(III) sulfate (CAN) to produce Compound 56. Finally, the protection groups in Compound 56 are removed with ammonia to produce Compound 57.

For radiolabeled compounds of the present invention, appropriate doses and routes of administration should be selected depending upon target diseases and objectives, but if they are used as an agent for diagnosis of tissue proliferation activity, a radioactivity in the range of 37 MBq to 740 MBq, preferably 111 MBq to 370 MBq is administered. Usually, they are administered intravenously, but in some cases, other routes of administration including arterial or intraperitoneal administration and direct administration to a tumor or other affected portions may be used.

If they are used as an agent for treatment of proliferative disease, a radioactivity in the range of 37 MBq to 7400 MBq, preferably 185 MBq to 3700 MBq, is administered. Usually, they are administered intravenously, but in some cases, other routes of administration including arterial or intraperitoneal administration and direct administration to a tumor or other affected portions may be used. Furthermore, if they are used for therapeutic purposes, the above dose may be administered several times at appropriate intervals.

The agent for diagnosis of tissue proliferation activity of the present invention can serve for whole-body or local scintigraphy and whole-body or local SPECT imaging by use of nuclides for SPECT. Using nuclides for PET, they can also be applied for whole-body or local PET imaging.

The agent for diagnosis of tissue proliferation activity of the present invention can serve for quantitative determination of local proliferative activity based on appropriate model analysis. Furthermore, if non-proliferation tissue is used as a control, local proliferative activity can be defined easily in a semi-quantitative way.

The agent for treatment of proliferative disease of the present invention, when a beta-emitter such as I-131 is used therein, can serves to decrease large tumors of 1 cm or more in diameter, depending on the range of the ray. When an alpha-emitter such as At-211 is used, they can work on small lesions of 0.1 mm or less in diameter more effectively than beta-emitter, and therefore, they are expected to serve for treatment of micrometastasis over the body. Furthermore, nuclides that emit Auger electrons, such as I-125, can have antitumor effects due to DNA breakage, only after labeled compounds have gathered around the DNAs. Therefore, suitable label nuclides for treatment of systemic tumor foci including metastatic ones include alpha-emitter such as At-211, and beta-emitter such as I-131 that can have effect on portions around the foci depending on the range. The most effective method is the cocktail therapy which uses a mixture of a compound labeled with an alpha-emitter and a compound labeled with a beta-emitter.

For treatment by local administration, compounds labeled with nuclides that emit Auger electrons, such as I-125, are particularly effective for brain tumor that is difficult to remove completely by surgical operation, and residual tumor from malignant melanoma, and in view of functional preservation, breast cancer, rectal cancer, prostatic cancer, and malignant mouth tumor, because they do no harm on portions other than pathologically proliferating cells owing to the properties of rays emitted therefrom. Technique for local administration includes, for example, an administration into intracavitary foci such as colon cancer by use of an endoscope, a direct administration to foci affected by brain tumor during craniotomy, and an administration by use of a catheter into an artery relevant to an affected organ such as liver affected by cancer.

EXAMPLES

The present invention will be described in detail below with reference to examples, but is not limited to these examples.

Example 1

Synthesis of 5-trimethylstannyl-4'-thio-2'-deoxyuridine (Compound 11)

Figure 1:
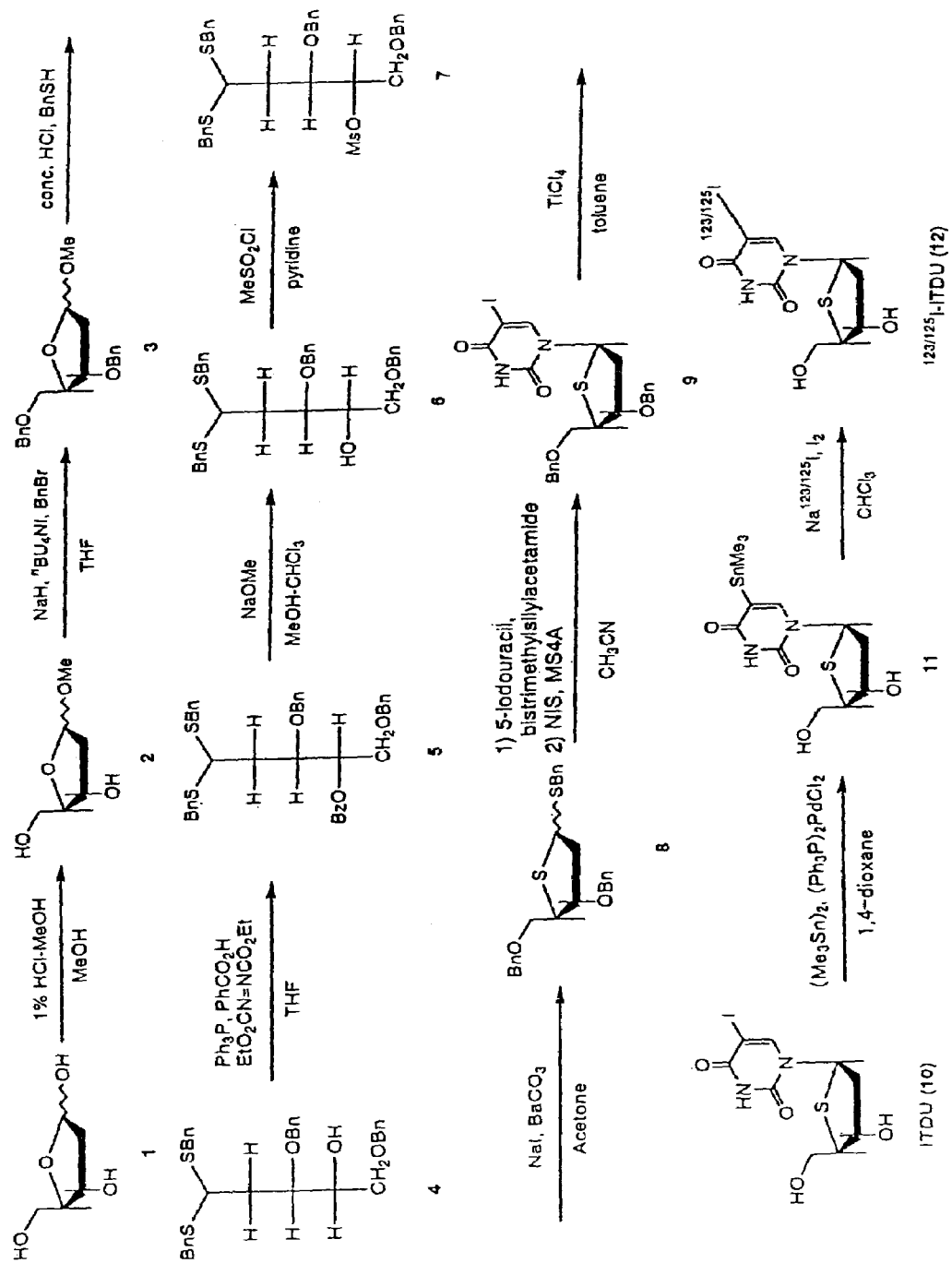
FIG. 1 illustrates a synthetic pathway for a compound of the present invention.

As shown in FIG. 1, benzyl-3,5-di-O-benzyl-2-deoxy-1,4-dithio-α,β-D-erythro-pentofuranoside (Compound 8) was synthesized, using 2-deoxy-D-erythro-pentose (Compound 1) as starting material, according to the method of Dyson M R et al. (Carbo. Res. 216, p.237 (1991)). Further, 5-iodo-4'-thio-2'-deoxyuridine (ITDU: Compound 10) was produced from Compound 8 according to the method of Oivanen M et al. (J. Chem. Soc., Perkin Trans. 2, p.2343 (1998)). Compound 10 was then used as a starting material to produce 5-trimethylstannyl-4'-thio-2'-deoxyuridine (Compound 11) according to the following procedure.

Compound 10 (9.5 mg, 0.026 mmol), bis(trimethyltin) (17.3 mg, 0.052 mmol) and bis(triphenylphosphine)palladium(II) chloride (5 mg) were dissolved in anhydrous 1,4-dioxane (3 mL) under argon atmosphere, and after heating at reflux for 3 hours, concentrated under reduced pressure. The residue was purified by silica gel thin layer chromatography (chloroform-methanol, 6:1) to produce the target Compound 11 (6.9 mg, 65%).

1H NMR (270 MHz, $CD_3OD$) δ 0.26 (s, 9H, $CH_3Sn$), 2.26 (ddd, 1H, J=4.6, 7.9, 13.2 Hz, 1H, H-2'), 2.27 (ddd, J=4.6, 6.6, 13.4 Hz, 1H, H-2'), 3.41 (m, 1H, H4'), 3.71 (dd, J=5.9, 11.2 Hz, 1H, H-5'), 3.80 (dd, J=4.6, 11.2 Hz, 1H, H-5'), 4.47 (q, J=4.0 Hz, 1H, H-3'), 6.41 (t, J=7.2 Hz, 1H, H-1'), 7.93 (s, 1H, H-5).

Example 2

Synthesis of [I-125]-5-iodo-4'-thio-2'-deoxyuridine ([I-125] ITDU: Compound 12)

To 0.1N sodium hydroxide solution (50 µL) of [I-125]-sodium iodide (33 MBq), water (1 mL) and chloroform (1 mL) were added, and then chloroform solution (4.7 µL) of iodine (60 µg, 0.47 µmol) was added, and shaken for 10 seconds. After removing only the aqueous layer, ethyl acetate solution (100 µL) of Compound 11 (100µg, 0.25 µmol) was added, and the resulting solution was left to stand at room temperature for 2 hours. One drop of 1N sodium thiosulfate solution was added, and chloroform was evaporated. After adding water (1 mL), the solution was passed through a Sep-Pak Plus QMA cartridge column. The column was washed with water (0.5 mL×2), and the resulting aqueous solution was combined to produce I-125-labeled Compound 12 (7.3 MBq, 22%).

Example 3

Synthesis of [I-123]-5-iodo-4'-thio-2'-deoxyuridine ([I-123] ITDU: Compound 12)

To 0.1% ammonium iodide solution (1 mL) containing [I-123]-ammonium iodide (2.0 GBq), 1N hydrochloric acid (0.1 mL) and chloroform (1 mL) were added, and then chloroform solution (4.7 µL) of iodine (60 µg, 0.47 µmol) was added, and shaken for 10 seconds. After removing only the aqueous layer, ethyl acetate solution (100 µL) of Compound 11 (100 µg, 0.25 µmol) was added and left to stand at room temperature for 2 hours. One drop of 1N sodium thiosulfate solution was added, and chloroform was evaporated. After adding water (1 mL), the solution was passed through a Sep-Pak Plus QMA cartridge column. The column was washed with water (0.5 mL×2), and the resulting aqueous solution was combined to produce I-125-labeled Compound 12 (228 MBq, 15%).

Example 4

Synthesis of 5-trimethylstannyl-1-(4-thio-D-arabinofuranosyl)uracil (Compound 21)

Figure 2:
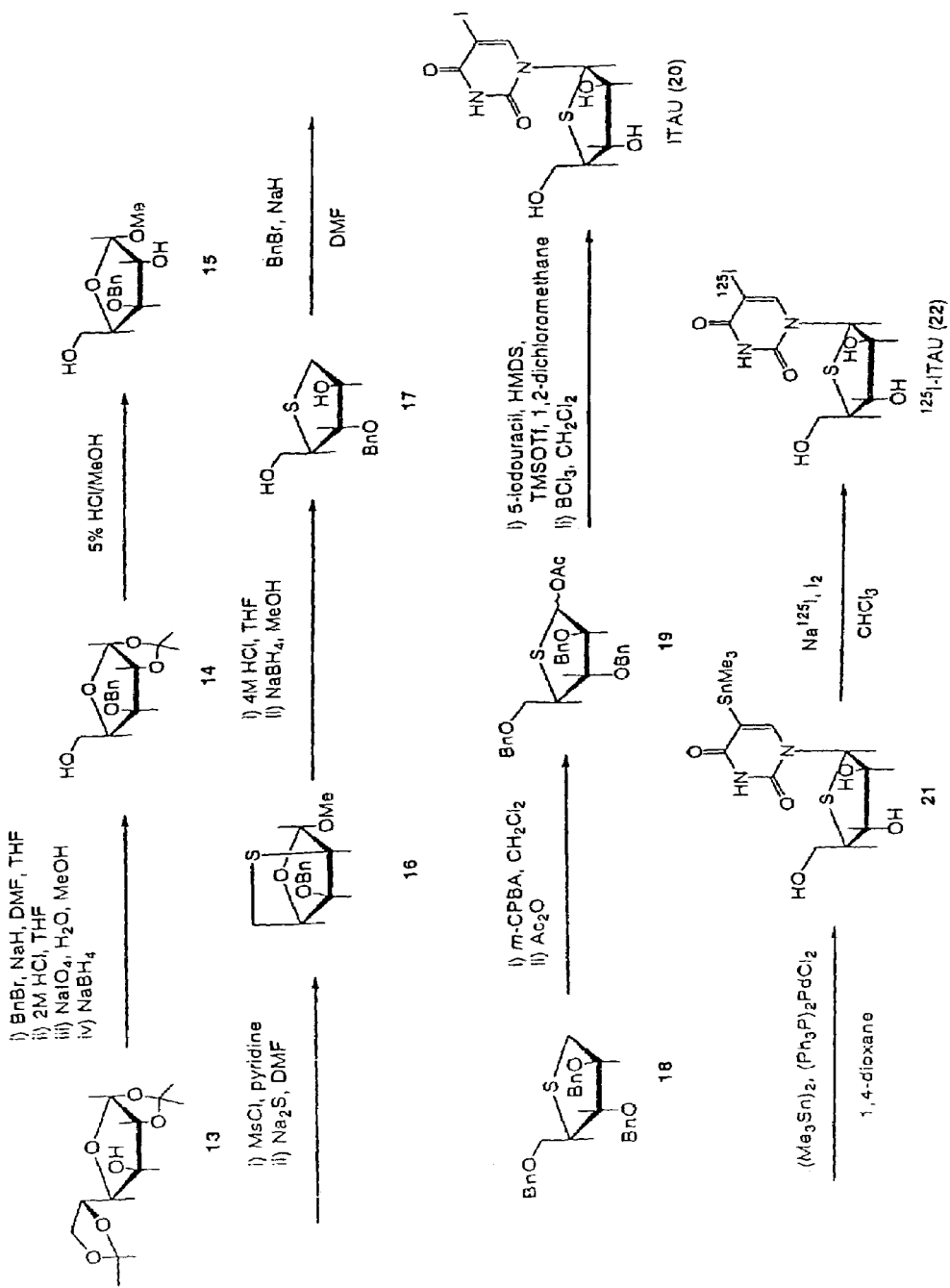
FIG. 2 illustrates another synthetic pathway for a compound of the present invention.
Figure 3:
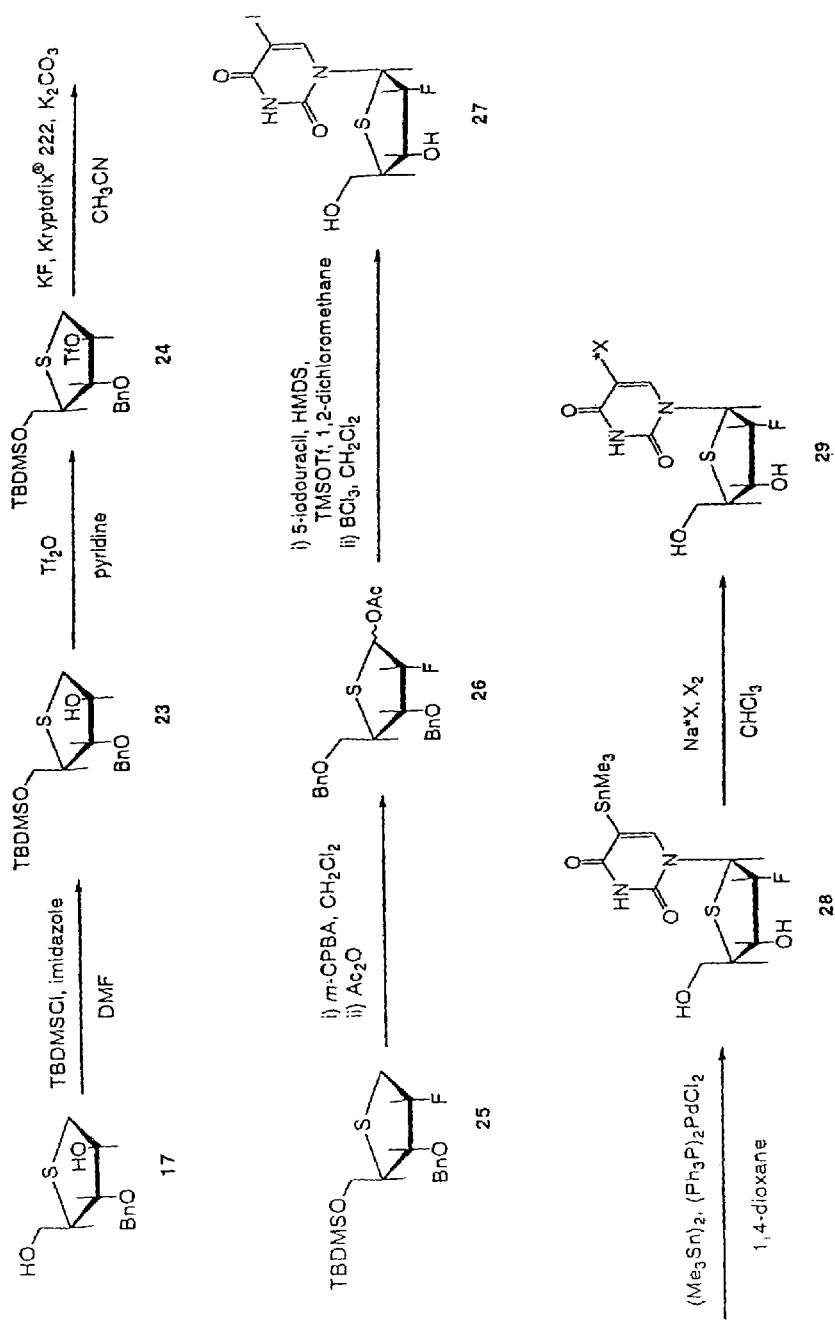
FIG. 3 illustrates a third synthetic pathway for a compound of the present invention.

As shown in FIG. 2, 1,4-anhydro-3-O-benzyl-4-thio-α-D-arabitol (Compound 17) was synthesized from 1,2;5,6-di-O-isopropylidene glucose (Compound 13) according to the method of Yoshimura Y et al. (J. Org. Chem. 61, p.822 (1996)). Then, 5-iodo-1-(4-thio-D-arabinofuranosyl)uracil (ITAU: Compound 20) was produced from Compound 17 according to the method of Yoshimura Y et al. (J. Med. Chem.40, p.2177 (1997)). This Compound 20 was used as a starting material, to produce 5-trimethylstannyl-1-(4-thio-D-arabinofuranosyl)uracil (Compound 21) by the following procedure.

Compound 20 (4.0 mg, 0.010 mmol), bis(trimethyltin) (6.6 mg, 0.020 mmol) and bis(triphenylphosphine)palladium(II) chloride (5 mg) were dissolved in anhydrous 1,4-dioxane (5 mL) in an argon atmosphere, and after heating at reflux for 4 hours, concentrated under a reduced pressure. The residue was purified by silica gel thin layer chromatography (25% methanol/chloroform) to produce the target Compound 21 (2.3 mg, 55%).

1H NMR (270 MHz, $CD_3OD$) δ 0.7 (s, 9H), 3.55–3.67 (m, 1H), 3.77–3.95 (m, 2H), 4.07 (t, J=5.9 Hz, 1H), 4.16 (t, J=5.9, 1H), 6.28 (d, J=5.3 Hz, 1H), 8.03 (s, 1H).

Example 5

Synthesis of [I-125]-5-iodo-1-(4-thio-D-arabinofuranosyl)uracil ([I-125] ITAU: Compound 22)

To 0.1N sodium hydroxide solution (50 μL) of [I-125]-sodium iodide (67 MBq), water (1 mL) and chloroform (1 mL) were added, and then chloroform solution (4.7 μL) of iodine (60 μg, 0.47 μmol) was added, and shaken for 10 seconds. After removing only the aqueous layer, ethyl acetate solution (100 μL) of Compound 21 (100 μg, 0.24 μmol) was added, and the resulting solution was left to stand at room temperature for 2 hours. One drop of 1N sodium thiosulfate solution was added, and chloroform was evaporated. After adding water (1 mL), the solution was passed through a Sep-Pak Plus QMA cartridge column. The column was washed with water (0.5 mL×2), and the resulting aqueous solution was combined to produce I-125-labeled Compound 22 (17.3 MBq, 26%).

Example 6

Synthesis of 5-trimethylstannyl-1-(2-deoxy-2-fluoro-β-D-arabinopentofuranosyl)uracil (Compound 40)

Figure 4:
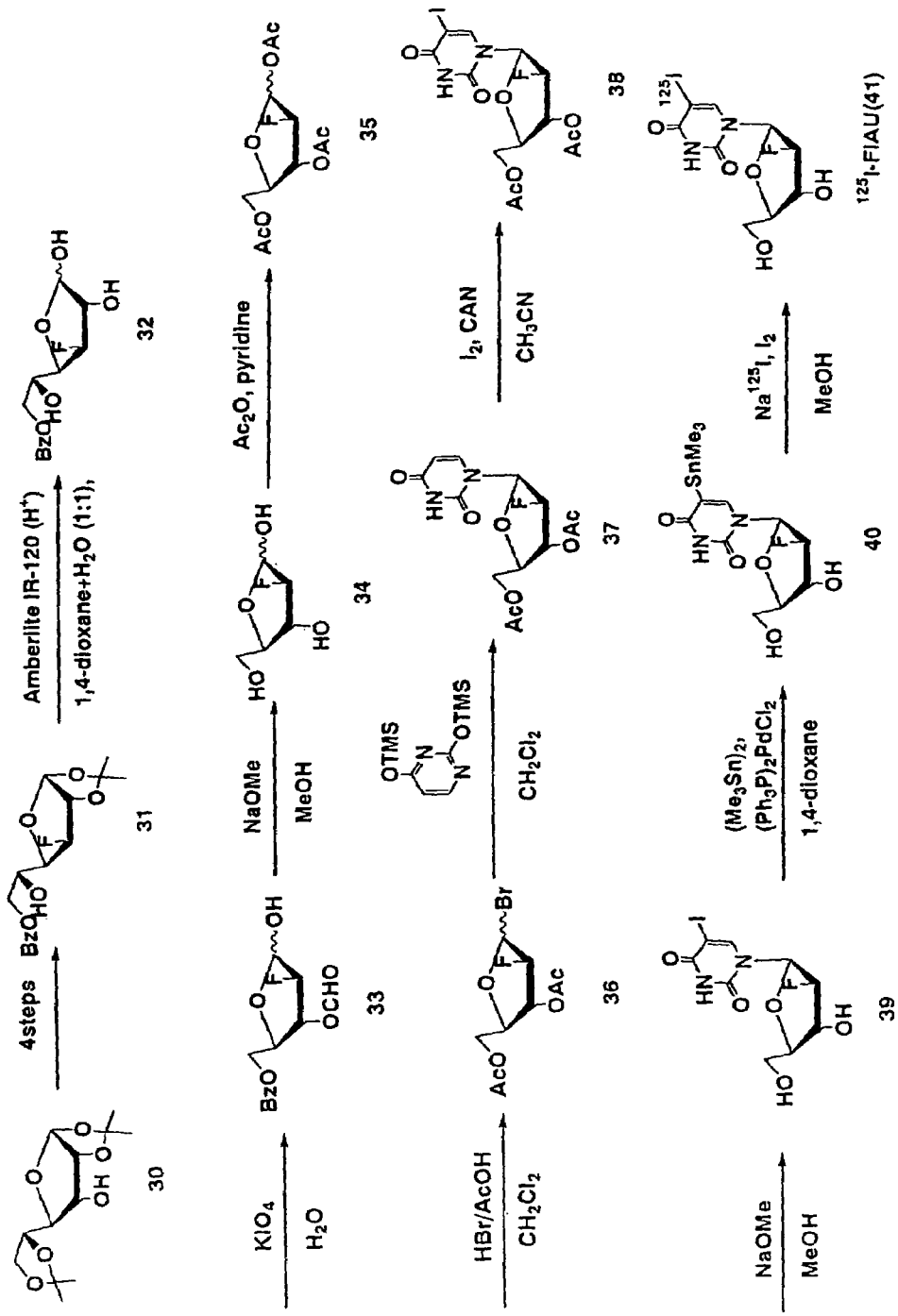
FIG. 4 illustrates a fourth synthetic pathway for a compound of the present invention (5-trialkyltin compounds) and [I-125] FIAU produced therefrom.

As shown in FIG. 4, 1-(3,5-di-O-acetyl-2-deoxy-2-fluoro-β-D-arabinopentofuranosyl)uracil (Compound 37) was synthesized from 1,2:5,6-di-O-isopylidene glucose (Compound 30) according to the method of Reichman U et al. (Carbohydrate Res. 42, p.233 (1975)). Further, 5-iodo-1-(2-deoxy-2-fluoro-β-D-arabinopentofuranosyl)uracil (Compound 39) was produced from Compound 37 according to the method of Asakura J et al. (J. Org. Chem.55, p.4928 (1990)). This compound was used as starting material to produce 5-trimethylstannyl-1-(2-deoxy-2-fluoro-β-D-arabinopentofuranosyl)uracil (Compound 40) by the following procedure.

Compound 39 (5.0 mg, 0.013 mmol), bis(trimethyltin) (20.5 mg, 0.063 mmol) and bis(triphenylphosphine)palladium(II) chloride (6.2 mg) were dissolved in anhydrous 1,4-dioxane (3 mL) in an argon atmosphere, and after heating at reflux for 2 hours, concentrated under a reduced pressure. The residue was purified by silica gel thin layer chromatography (chloroform-methanol, 6:1) to produce the target Compound 40 (3.6 mg, 66%).

1H-NMR(500 MHz, CD$_3$OD) δ 0.25 (S, 9H, CH$_3$Sn), 3.72 (dd, J=5.0, 12.0 Hz, 1H, H-5'), 3.79–3.91 (m, H-4'), 4.33 (ddd, J=3.0, 5.0, 18.5 Hz, 1H, H-3'), 5.02 (td, J=4.0, 53.0 Hz, 1H, H-2'), 6.25 (dd, J=4.5, 16.0 Hz, 1H, H-1'), 7.56 (S, 1H, H-5).

Example 7

Synthesis of [I-125]-5-iodo-1-(2-deoxy-2-fluoro-β-D-arabinopentofuranosyl)uracil ([I-125] FIAU: Compound 41)

First, 0.1N sodium hydroxide solution of [I-125]-sodium iodide (80 MBq) was distilled off, followed by addition of methanol (1 mL), addition of methanol solution (4.8 μL) of iodine (61 μg, 0.481 μmol), and shaking for 10 seconds. Then, methanol solution (100 μL) of Compound 40 (100 μg, 0.24 μmol) was added, and the solution was left to stand at room temperature for 2 hours. One drop of 1N sodium thiosulfate solution was added, and methanol was evaporated. After adding water (1 mL), the solution was passed through a Sep-Pak Plus QMA cartridge column. The column was washed with water (1.0 mL), and the resulting aqueous solution was combined to obtain I-125-labeled Compound 41 (9.5 MBq, 12%).

Example 8

Synthesis of 5-trimethylstannyl-1-(2-deoxy-2-fluoro-4-thio-β-D-arabinopentofuranosyl)uracil (Compound 50)

Figure 5:
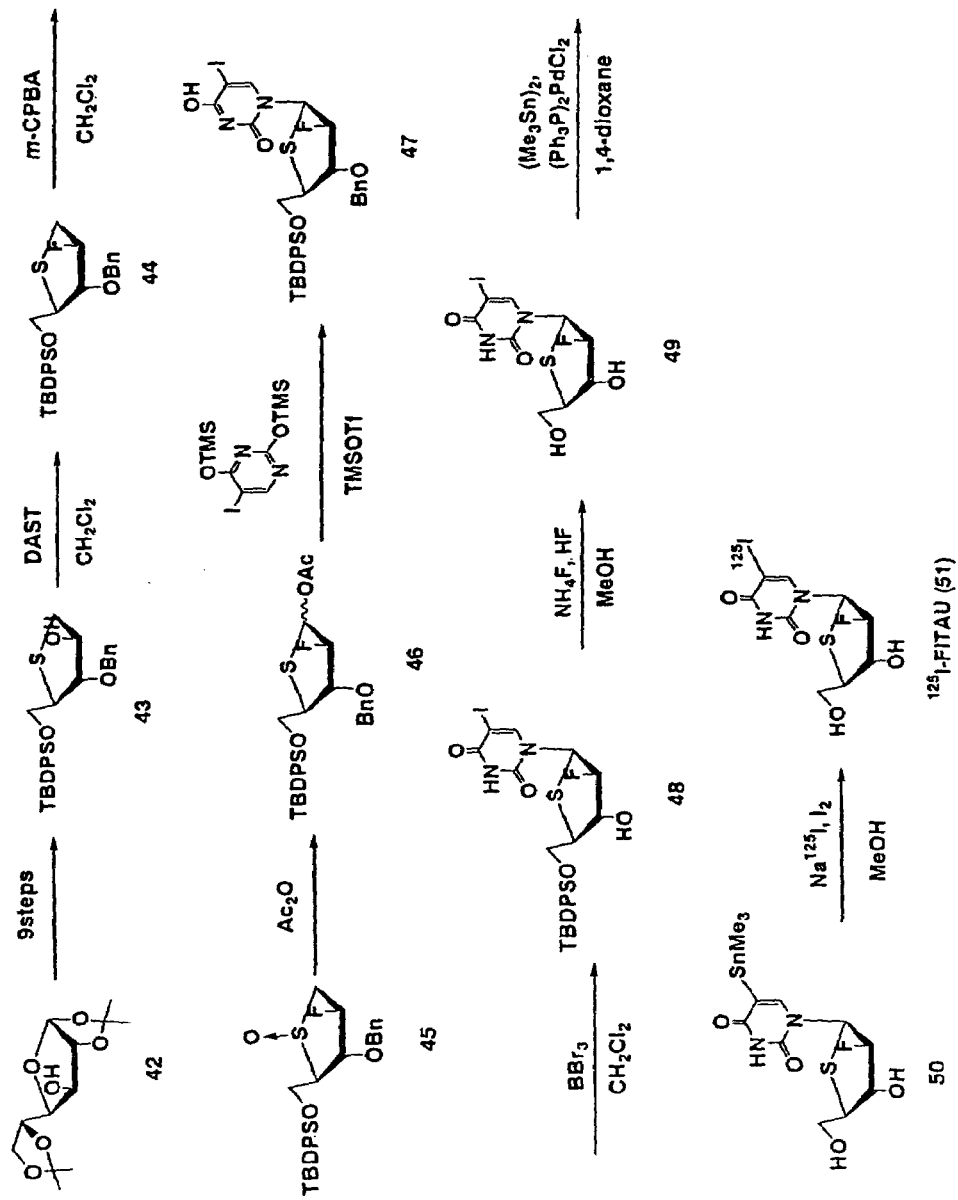
FIG. 5 illustrates a fifth synthetic pathway for a compound of the present invention.

As shown in FIG. 5, 1-O-acetyl-3-O-benzyl-5-O-(tert-butyldiphenylsilyl)-2-deoxy-2-fluoro-4-thio-D-arabinopentofuranose (Compound 46) was synthesized from 1,2:5,6-di-O-isopylidene glucose (Compound 42) according to the method of Yoshimura Y et al. (J. Org. Chem.62, p.3140 (1997)). Further, Compound 46 was used to produce 5-iodo-1-(2-deoxy-2-fluoro-4-thio-β-D-arabinopentofuranosyl)uracil (Compound 49) according to the method of Yoshimura Y et al. (Bioorg. Med. Chem.8, p.1545 (2000)). This compound was then used as a starting material to produce 5-trimethylstannyl-1-(2-deoxy-2-fluoro-4-thio-β-D-arabinopentofuranosyl)uracil (Compound 50) by the following procedure.

Compound 49 (5.0 mg, 0.013 mmol), bis(trimethyltin) (16.9 mg, 0.052 mmol) and bis(triphenylphosphine)palladium(II) chloride (6.0 mg) were dissolved in anhydrous 1,4-dioxane (3 mL) in an argon atmosphere, and after heating at reflux for 3.5 hours, concentrated under reduced pressure. The residue was purified by silica gel thin layer chromatography (chloroform-methanol, 6:1) to produce the target Compound 50 (1.9 mg, 35%).

1H-NMR (500 MHz, CD$_3$OD) δ 0.26 (S, 9H, CH$_3$Sn), 3.61–3.68 (m, 1H, H-5'), 3.80–3.81 (m, H-4'), 4.37 (td, J=6.0, 12.0 Hz, 1H, H-3'), 4.97 (td, J=5.5, 49.0 Hz, 1H, H-2'), 6.46 (dd, J=5.5, 11.5 Hz, 1H, H-1'), 7.99 (S, 1H, H-5).

Example 9

Synthesis of [I-125]-5-iodo-1-(2-deoxy-2-fluoro-4-thio-β-D-arabinopentofuranosyl)uracil ([I-125] FITAU: Compound 51)

First, 0.1N sodium hydroxide solution of [I-125]-sodium iodide (45 MBq) was distilled off, followed by addition of methanol (1 mL), addition of methanol solution (4.8 μL) of iodine (61 μg, 0.48 μmol), and shaking for 10 seconds. Then, methanol solution (100 μL) of Compound 50 (100 μg, 0.24 μmol) was added, and the resulting solution was left to stand at room temperature for 2 hours. One drop of 1N sodium thiosulfate solution was added, and methanol was evaporated. After adding water (1 mL), the solution was passed through a Sep-Pak Plus QMA cartridge column. The column was washed with water (1.0 mL), and the resulting aqueous solution was combined to obtain I-125-labeled Compound 51 (3.5 MBq, 7.8%).

Example 10

Synthesis of 5-trimethylstannyl-1-methyl(2-deoxy-2-bromo-β-D-arabinopentofuranosyl)uracil ([I-125] IMBAU: Compound 58)

Figure 6:
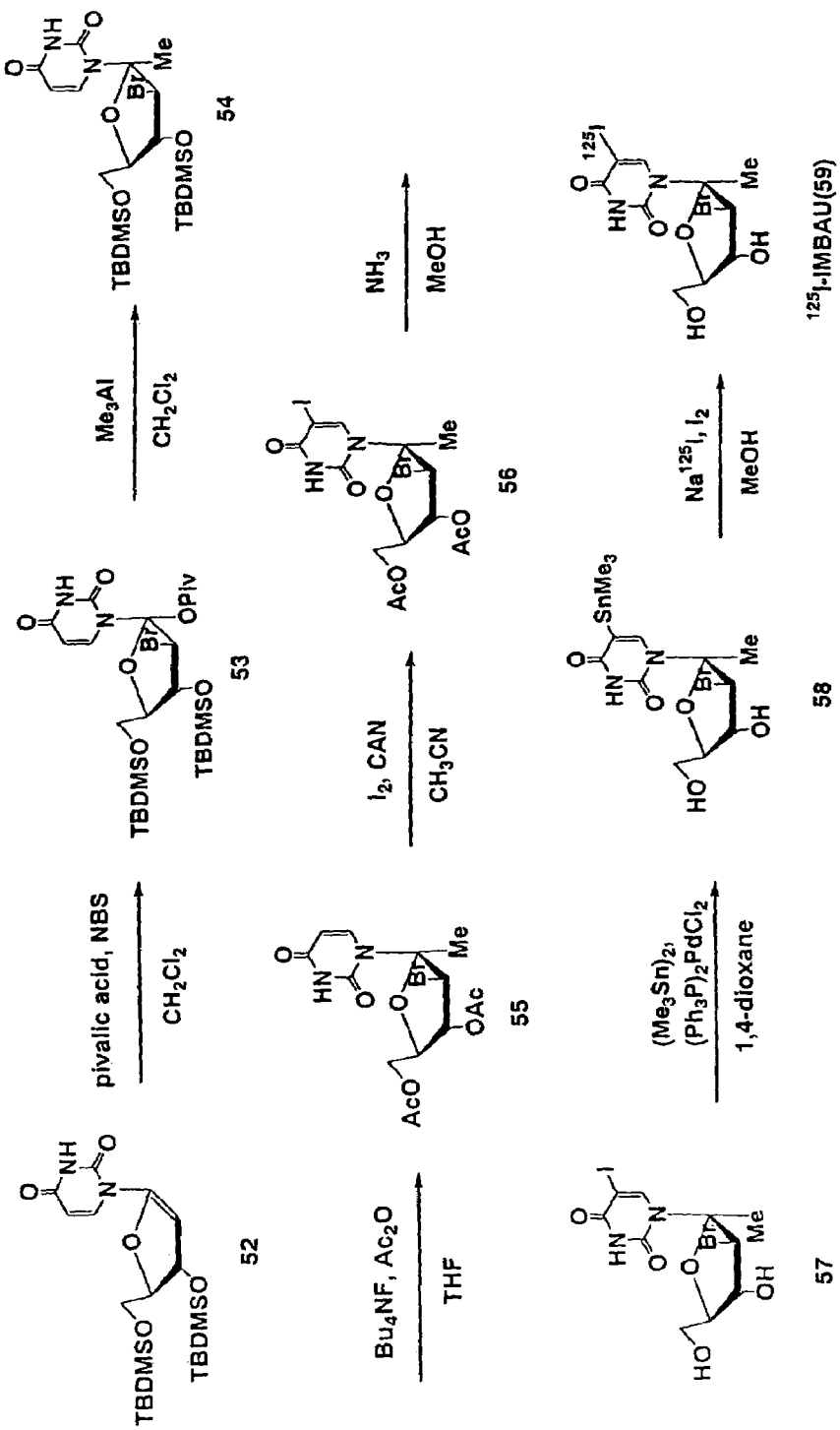
FIG. 6 illustrates the other synthetic pathway for a compound of the present invention.

As shown in FIG. 6, 1-[2-bromo-3,5-bis-O-(tert-butyldimethylsilyl)-2-deoxy-1-C-methyl-β-D-arabinofuranosyl]uracil (Compound 54) was produced from 1-[3,5-bis-O-(tert-butyldimethylsilyl)-2-deoxy-D-erythro-pento-1-enofuranosyl]uracil (Compound 52) according to the method of Itoh Y et al. (J. Org. Chem. 60, p.656 (1995)). Further, 5-iodo-1-methyl(2-deoxy-2-bromo-β-D-arabinopentofuranosyl)uracil (Compound 57) was produced from Compound 54 according to the method of Asakura J et al. (J. Org. Chem. 55, p.4928 (1990)). This compound was used as starting material to produce 5-trimethylstannyl-1-methyl(2-deoxy-2-bromo-β-D-arabinopentofuranosyl)uracil (Compound 58) by the following procedure.

Compound 57 (4.9 mg, 0.01 mmol), bis(trimethyltin) (16.0 mg, 0.049 mmol) and bis(triphenylphosphine)palladium(II) chloride (5 mg) were dissolved in anhydrous 1,4-dioxane (3 mL) in an argon atmosphere, and after heating at reflux for 2.5 hours, concentrated under a reduced pressure. The residue was purified by silica gel thin layer chromatography (chloroform-methanol, 6:1) to produce the target Compound 58 (3.8 mg, 72%).

1H NMR (500 MHz, CD$_3$OD) δ 0.25 (S, 9H, CH$_3$Sn), 1.95 (S, 3H, 1'-CH$_3$), 3.61–3.70 (m, 2H, H-5'), 4.08–4.11 (m, 1H, H-4'), 4.53 (d, J=3.0 Hz, 1H, H-5'), 4.79 (S, 1H, H-2'), 7.75 (S, 1H, H-5).

Example 11

Synthesis of [I-125]-5-iodo-1-methyl-(2-deoxy-2-bromo-β-D-arabinopentofuranosyl)uracil ([I-125] IMBAU: Compound 59)

First, 0.1N sodium hydroxide solution of [I-125]-sodium iodide (62 MBq) was distilled off, followed by addition of methanol (1 mL), addition of methanol solution (4.0 μL) of iodine (51 μg, 0.40 μmol), and shaking for 10 seconds. Then, methanol solution (100 μL) of Compound 58 (100 μg, 0.20 μmol) was added, and the resulting solution was left to stand at room temperature for 2 hours. One drop of 1N sodium thiosulfate solution was added, and methanol was evaporated. After adding water (1 mL), the solution was passed through a Sep-Pak Plus QMA cartridge column. The column was washed with water (1.0 mL), and the resulting aqueous solution was combined to obtain I-125-labeled Compound 59 (8.3 MBq, 13%).

Example 12

Test for in vitro Phosphorylation Activity of [I-125] ITDU and [I-125] ITAU

The phosphorylation activity of a labeled compound by thymidine kinase was determined using a crude enzyme extracted from a mouse's lung cancer cell strain LL/2. Liquid enzyme was extracted from a LL/2 mouse's lung cancer cell strain in the logarithmic growth phase according to the method of Wolcott R M and Colacino J M (Anal. Biochem 178, p.38–40 (1989)). To a reaction liquid containing ATP, which is a phosphate donor, 2 nmole of the label compound and the liquid enzyme were added and reacted at 37° C. for a fixed period of time. The reaction was stopped by adding 1 mL of a 100 mM lanthanum chloride/5 mM triethanolamine solution. Phosphorylated material was prepared by centrifugal separation to form a phosphate-metal complex, followed by measuring a radioactivity of the resulting precipitate with an automatic well-type gamma counter (ARC-380, Aloka Co., Ltd.). Results are shown in Table 1 from which phosphorylation activity attributed to thymidine kinase was confirmed in both [I-125] ITDU and [I-125] ITAU.

TABLE 1

Phosphorylation activity of iodo-labeled nucleic acid derivatives (n = 3)

| Iodo-labeled nucleic acids | Phosphorylated material production rate (p mole/mg protein/h) |
|---|---|
| [I-125]ITDU | 1182.7 ± 100.1 |
| [I-125]ITAU | 13.6 ± 6.6 |

Example 13

Test for in vitro Metabolic Stability of [I-125] ITDU and [I-125] ITAU

To evaluate metabolic stability of glycosidic bond, decomposition reactivity for E. coli-originating thymidine phospholylase was studied. To the reaction liquid, 2 nmole of the labeled compound and 9 units of a liquid enzyme (Sigma Corporation) were added and reacted at 25° C. for a fixed period of time, and the reaction was stopped by treatment in a boiling water bath for 3 minutes. The reaction liquid was subjected to centrifugal separation, and the supernatant was applied over a thin layer silica gel plate along with an authentic standard (5-iodouridine: IU) and a non-labeled parent compound. It was developed with a mixture of chloroform and isopropyl alcohol (3:1), and then autoradiography was measured with a bioimaging analyzer (BAS-1500, Fuji Photo Film Co., Ltd.). The area of interest was set to peak components of the Rf value corresponding to the authentic standard, and the amount of the resulting metabolite was calculated from its proportion in percentage. Results are shown in Table 2 which indicates that [I-125] ITDU and [I-125] ITAU are stabler than 5-iododeoxyuridine ([I-125] IUR).

TABLE 2

C—N glycosidic bond cleavage activity for iodo-labeled nucleic acid derivatives (n = 3)

| Iodo-labeled nucleic acids | 5-iodouridine production rate* (relative activity) |
|---|---|
| [I-125]IUR | 138606.2 ± 14902.3 (1.00) |
| [I-125]ITDU | 4075.9 ± 736.4 (0.03) |
| [I-125]ITAU | 524.3 ± 373.8 (<0.01) |

*p mole/units/30 min

Example 14

Evaluation of in vitro Stability of Metabolism of Various Radioactive-iodine-labeled Nucleic Acid Derivatives by Thymidine Phospholylase To evaluate the metabolic stability of glycosidic bond in various radioactive iodine-labeled nucleic acid derivatives, their decomposition reactivity for E. coli-originating thymidine phospholylase was studied. To the reaction liquid, 0.5–12.0 nmol of the labeled compound and 0.0009–9.0 units of a liquid enzyme (Sigma Corporation) was added and reacted at 25° C. for a fixed period of time, followed by treatment in a boiling water bath for 3 minutes to stop the reaction. As [I-125] IBMAU is unstable under heat treatment, the reaction liquid was cooled with ice to stop the reaction. The reaction liquid was subjected to centrifugal separation, and the supernatant was applied over a silica gel plate along with an authentic standard (5-iodouridine: IU) and a non-labeled parent compound. It was developed with a mixture of chloroform and isopropyl alcohol (3:1), and then the autoradiogram was measured with a bioimaging analyzer (BAS-1500, Fuji Photo Film Co., Ltd.). The area of interest was set to peak components of the Rf value corresponding to the authentic standard, and the amount of the resulting metabolite was calculated from its proportion in percentage. In the case of [I-125] FITAU and [I-125] IMBAU, a reversed phase silica gel plate was used, and after development with a mixture of methanol and water (3:7), an autoradiogram was measured with a bioimaging analyzer (BAS-1500; Fuji Photo Film Co., Ltd.) similarly to the [I-125] IUR and others. Results of analysis are shown in Table 3 which indicates that [I-125] FITAU and [I-125] IMBAU are still stabler than [I-125] IUR.

TABLE 3

C—N glycosidic linkage cleavage activity of iodo-labeled nucleic acid derivatives by thymidine phospholylase for (n = 3)

| Iodo-labeled nucleic acids | 5-IU production rate (pmol/units/0.5 h) | Relative activity |
|---|---|---|
| [I-125]IUR | 138606.2 ± 14902.3 | 1.00 |
| [I-125]ITdU | 3778.7 ± 692.0 | 0.03 |
| [I-125]ITAU | 514.8 ± 367.0 | <0.01 |
| [I-125]FITAU | 0.5 ± 0.1 | <0.00001 |
| [I-125]IMBAU | 0.0 | 0.0 |

Example 15

Test of Thymidine Kinase-dependent Incorporation into Celles Using Thymidine Kinase-deficient Cells Thymidine kinase-dependent incorporation of labeled compounds into cells was studied based on difference in incorporation between thymidine kinase-deficient cell strains L-M (TK-) and their parent L-M cells. L-M and L-M (TK-) cells in the logarithmic growth phase were planted on 24-well plates, each carrying $2.0 \times 10^5$ cells, and cultured overnight. Then 2 nmol of a radioactive iodine-labeled nucleic acid derivative was added and allowed to be incorporated in the cells for one hour. The cells were washed three times with an ice-cooled phosphate buffer solution, and dissolved in 0.1N NaOH, followed by determination of degree of radioactivity incorporated in the cells using an automatic well-type gamma counter (ARC-380 or ARC-300, Aloka Co., Ltd.). Measurements were analyzed to make evaluations based on the amount of the incorporated label molecules per unit weight of cellular proteins. Results are shown in Table 4 which indicates that [I-125] ITdU and [I-125] FITAU were incorporated in cells in a thymidine kinase dependent way as in the case of the [I-125] IUR as a control.

TABLE 4

Incorporation of radioactive iodine-labeled nucleic acids in L-M and L-M (TK-) cells

| Iodo-labeled nucleic acids | Incorporation (pmol/mg protein/h) | | (L-M)/ {L-M(TK-)} |
|---|---|---|---|
| | L-M | L-M (TK-) | |
| [I-125] IUR | 77.80 ± 7.45 | 27.86 ± 2.94 | 2.79* |
| [I-125] ITdU | 10.90 ± 1.48 | 3.94 ± 0.63 | 2.77* |
| [I-125] ITAU | 1.68 ± 0.28 | 1.20 ± 0.20 | 1.40** |
| [I-125] FITAU | 0.34 ± 0.05 | 0.21 ± 0.05 | 1.62*** |

*p < 0.0005,
**p < 0.05,
***p < 0.01(T-test)

Example 16

Test for in vivo Label Stability of [I-125] ITDU and [I-125] ITAU

Figure 7:
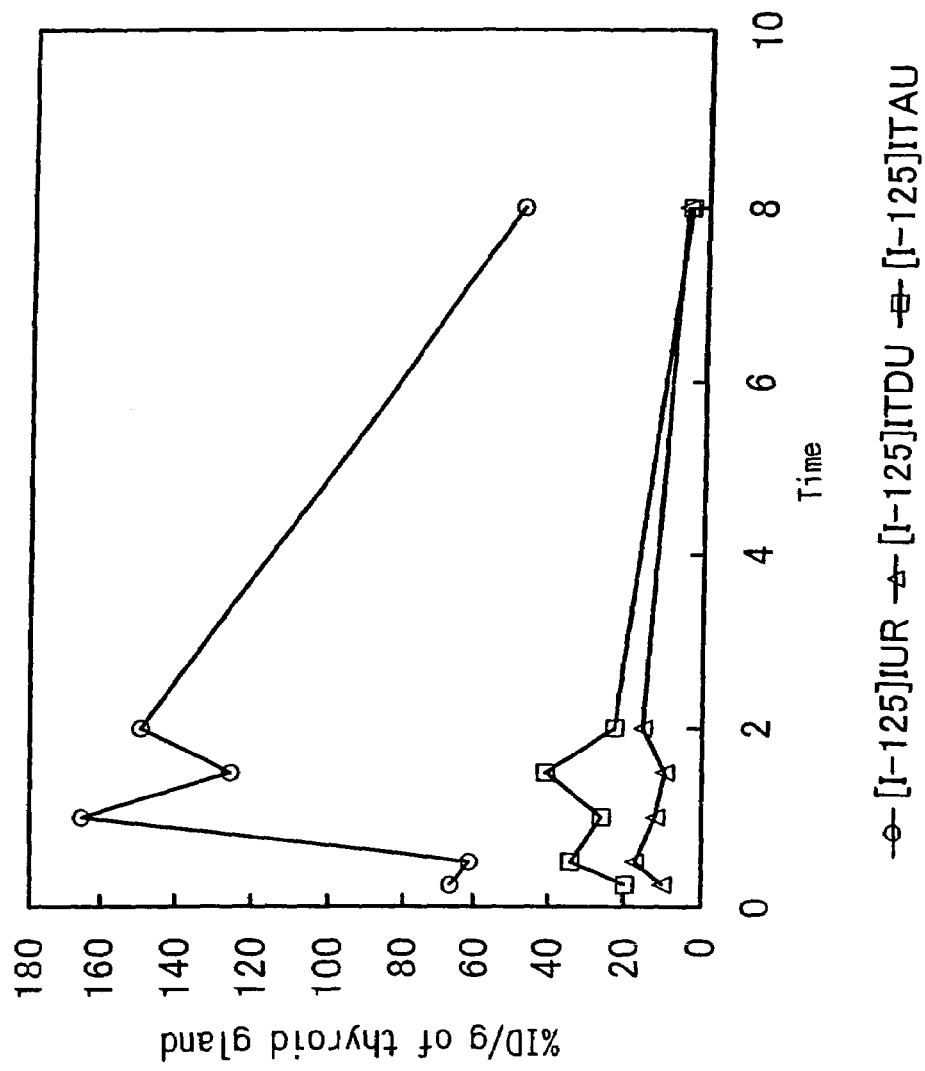
FIG. 7 illustrates a diagram showing in vivo label stability of [I-125] ITDU and [I-125] ITAU measured in Example 16, along with [I-125] IUR as a control.

To evaluate in vivo label stability of [I-125] ITDU and [I-125] ITAU, tests were conducted to study the accumulation of free iodine in the thyroid gland in normal mice. A 370 KBq portion of each labeled compound was injected in each of 10 week old normal mice into its tail vein, and three animals were sacrificed and anatomized at appropriate intervals. For a control, in vivo distribution of [I-125] IUR was also observed. Incorporation of radioactivity in the thyroid gland was measured with an automatic well-type gamma counter (ARC-300, Aloka Co., Ltd.). Incorporated radioactivity in tissue was calculated as the administrated dose per gram of the tissue per unit time, and represented in percentage, as shown in FIG. 7. Results indicate that the accumulated radioactivity from [I-125] ITDU and [I-125] ITAU in the thyroid gland was significantly smaller than that from the control [I-125] IUR, proving that the in vivo label stability of the agents is high.

Example 17

In vivo Label Stability of Radioactive Iodine-labeled Nucleic Acid Derivatives

Figure 8:
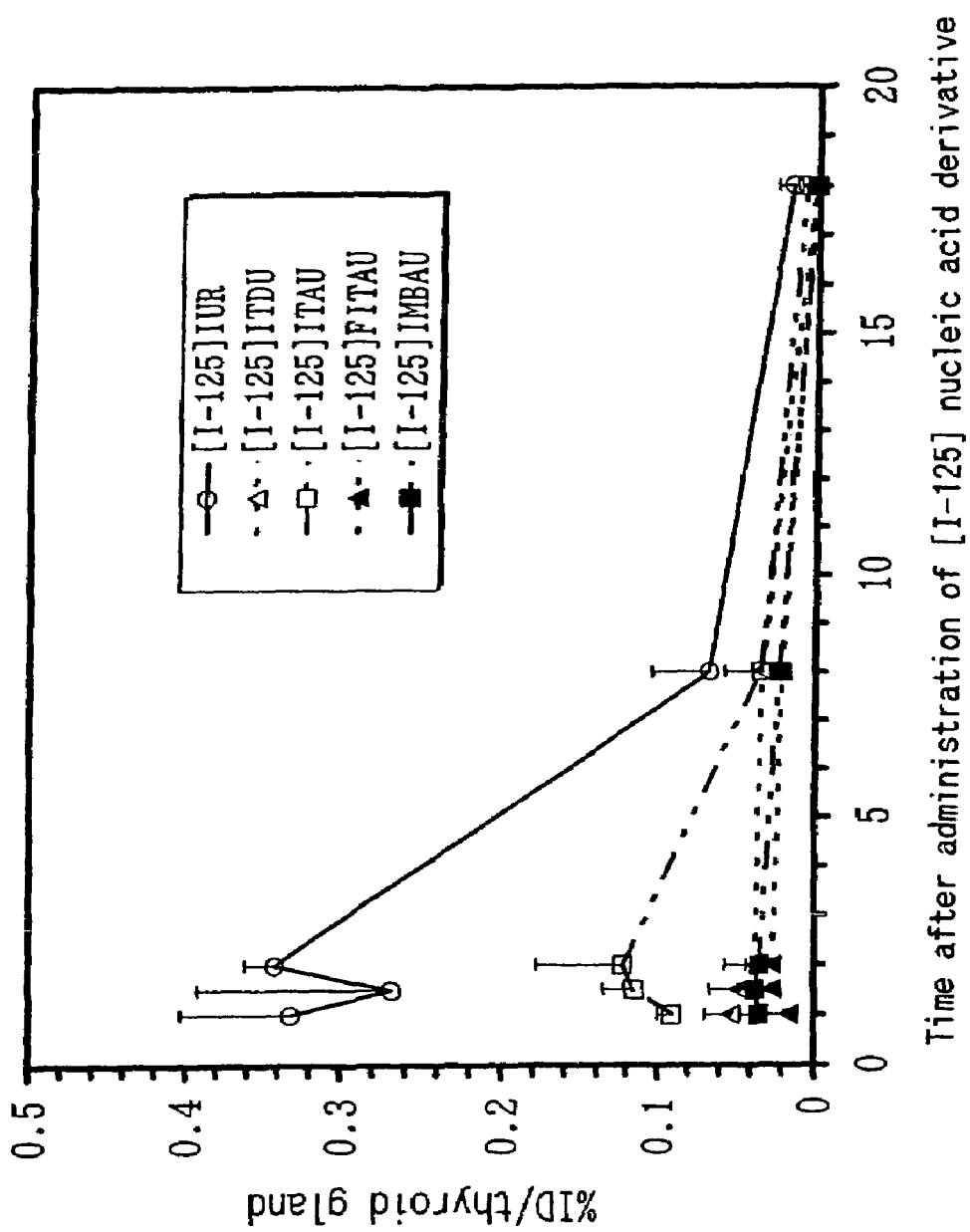
FIG. 8 illustrates a diagram showing in vivo label stability of [I-125] ITDU, [I-125] ITAU, [I-125] FITAU and [I-125] IMBAU measured in Example 17, along with [I-125] IUR (highly decomposable) as a control.

To evaluate in vivo stability of deiodination against each radioactive iodine-labeled nucleic acid derivative, tests were conducted to study accumulation of free iodine in the thyroid gland of normal mice. A 185 KBq of each labeled compound was injected in each of 10 week old normal mice (C57BL/6) into the tail vein, and three animals were sacrificed and anatomized at intervals longer than in Example 16. Incorporation of radioactivity in the thyroid gland was measured with an automatic well-type gamma counter (ARC-300, Aloka Co., Ltd.). Incorporated radioactivity in tissue (% ID) was calculated as the administrated per gram of the tissue, and represented in percentage, as shown in FIG. 8. Results indicate that the accumulated radioactivity from [I-125] ITDU, [I-125] ITAU, [I-125] FITAU and [I-125] IMBAU in the thyroid gland was significantly smaller than that from the control [I-125] IUR (highly metabolizable substance), proving that the in vivo label stability of the agents is high.

Example 18

In vivo Distribution of [I-125] ITDU in Normal Mice

Figure 9:
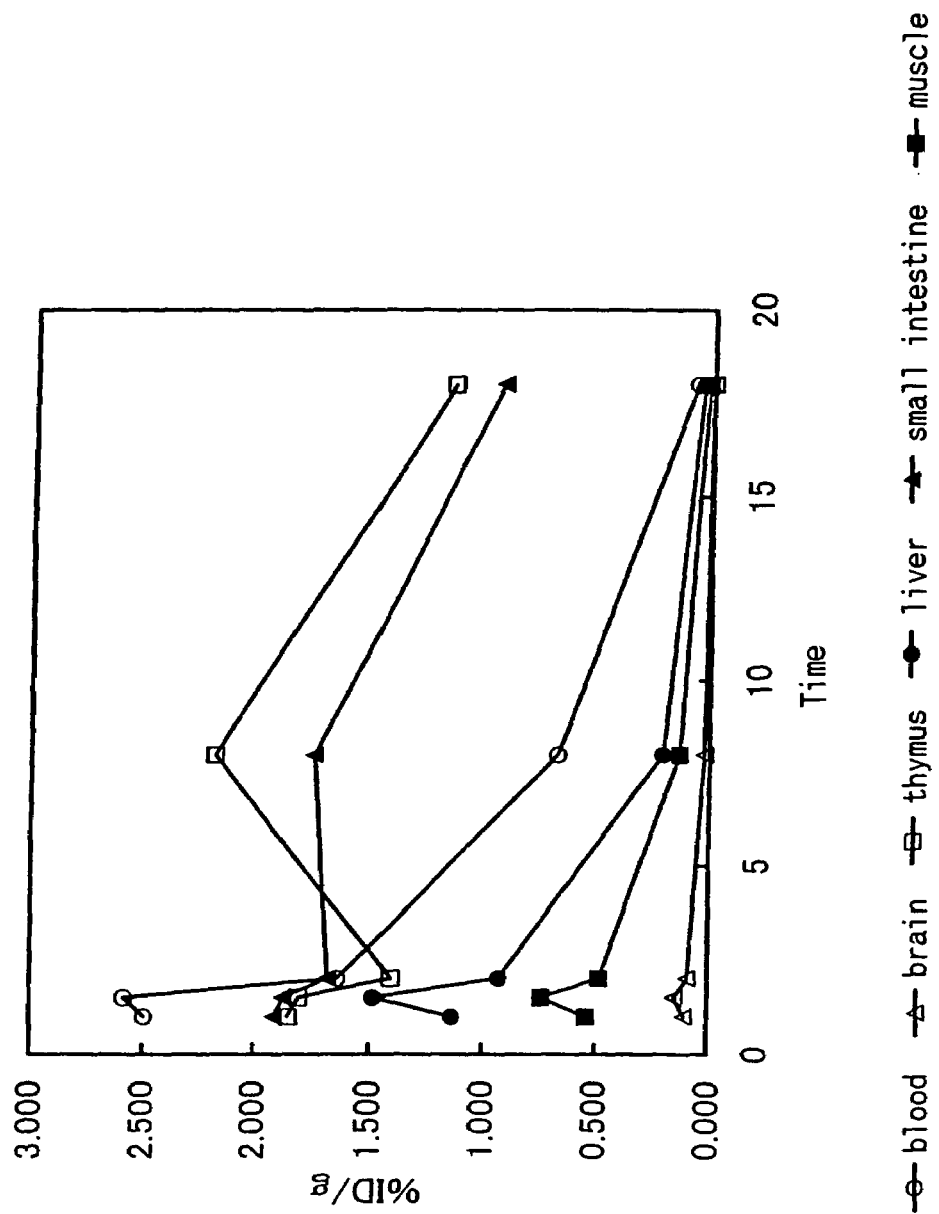
FIG. 9 illustrates a diagram showing in vivo distribution of [I-125] ITDU in normal mice measured in Example 18.

A 370 KBq of [I-125] ITDU was injected in each of 10 week old normal mice into the tail vein, and three animals were sacrificed and anatomized at appropriate intervals. Incorporation of radioactivity in each tissue sample was measured with an automatic well-type gamma counter (ARC-300, Aloka Co., Ltd.). Incorporated radioactivity in tissue was calculated as the administrated dose per gram of the tissue, and represented in percentage, as shown in FIG. 9. Results indicate that the accumulated radioactivity in proliferating tissues, namely the thymus and the small intestine, was certainly higher than that in non-proliferating tissues, namely the brain, liver and muscle.

Figure 10:
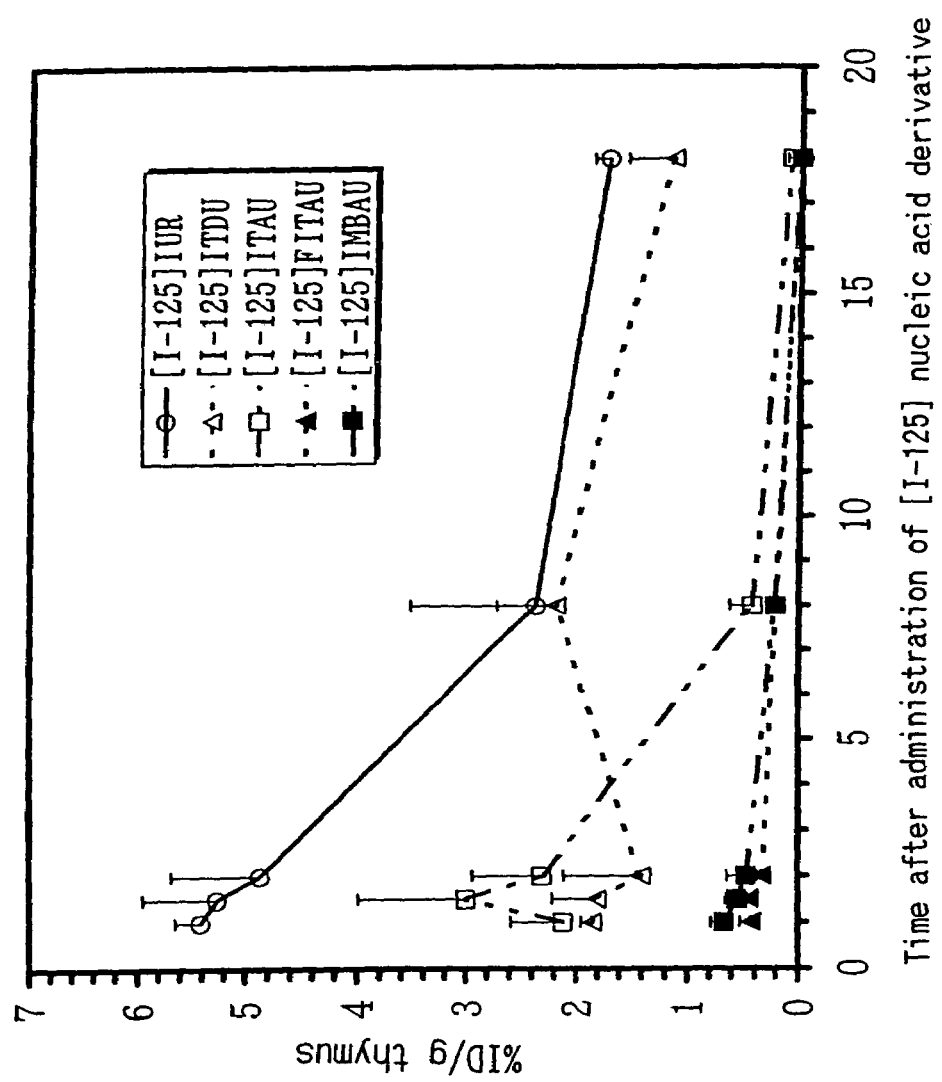
FIG. 10 illustrates a diagram showing in vivo accumulation of [I-125] ITDU, [I-125] ITAU, [I-125] FITAU and [I-125] IMBAU, along with [I-125] IUR as a control, in proliferating tissue measured in Example 18.

To evaluate the accumulation of each radioactive iodine-labeled nucleic acid derivative in proliferating tissues, tests were conducted to study in vivo distribution in normal mice. A 185 MBq of each labeled compound was injected in each of 10 week old normal mice (C57BL/6) through its tail vein, and three animals were sacrificed and anatomized at appropriate intervals. Incorporation of radioactivity in each tissue sample was measured with an automatic well-type gamma counter (ARC-300, Aloka Co., Ltd.). Incorporated radioactivity in tissue was calculated as the administrated dose per unit weight of the tissue, and represented in percentage (% ID/g). As shown in FIG. 10, results indicate that [I-125] IUR (positive control) and [I-125] ITDU have accumulated in large amounts particularly in the thymus which is a proliferating tissue in normal young mice.

Example 19

Sintigraphy of Walker Tumor Using [I-123] ITDU

Figure 11:
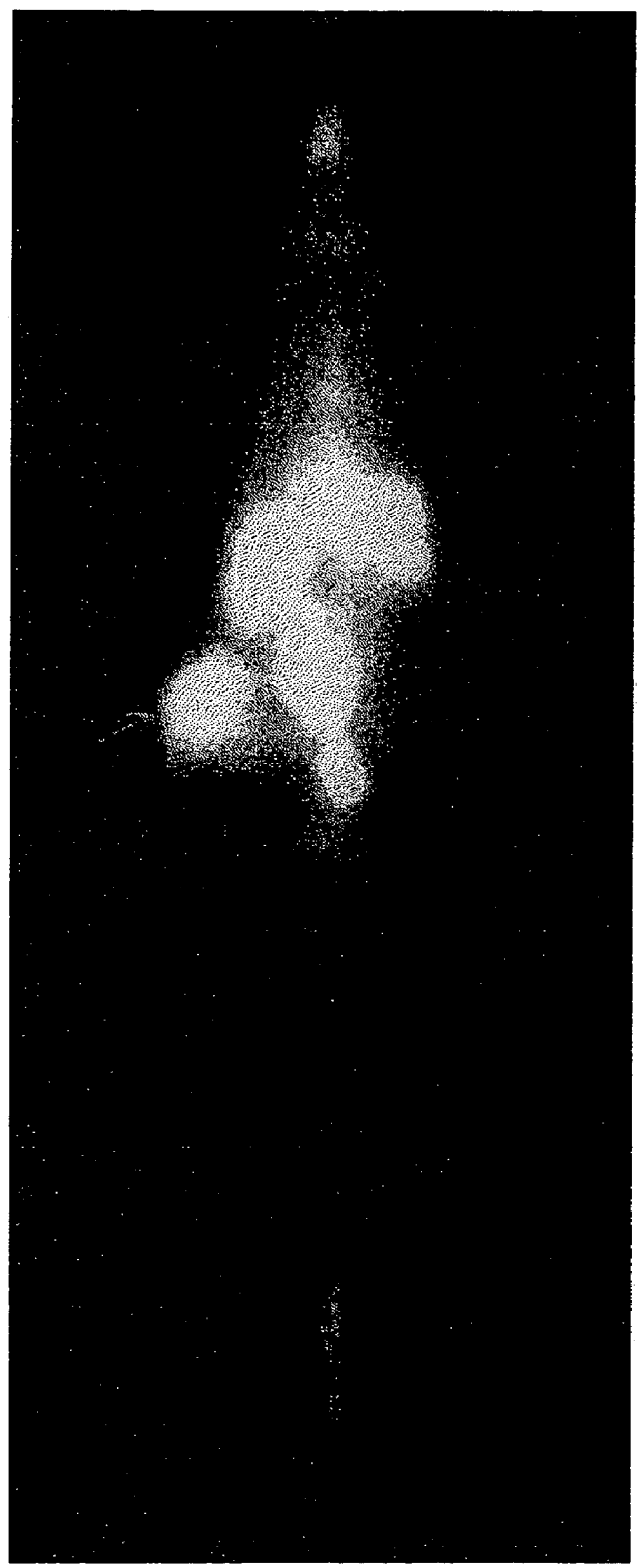
FIG. 11 illustrates a photograph (biological morphology) showing a scintigram of Walker tumor observed in Example 19.

Malignant tumor, a typical proliferative disease, was observed by scintigraphy. Walker tumor cells were transplanted subcutaneously in the right inguinal region of Wistar rats. After the transplantation, 37 MBq of [I-123] ITDU was injected into the tail vein of rats that suffered a palpable tumor of about 20 mm that was suitable for scintigraphy. Each tumor-transplanted rat was anesthetized with Ravonal four hours after the administration of a drug. Then the rat was fixed in the face-up position and observed statically with gamma-camera imaging equipment (GCA-90B, Toshiba Corporation). Imaging was performed using a high-resolution medium-energy collimator to obtain images for 10 minutes with a resolution of 256×256. Results are illustrated in FIG. 11 which shows that [I-123] ITDU serves for clear imaging of transplanted tumors (indicated by an arrow) in Wister rats.

INDUSTRIAL APPLICABILITY

The radiolabeled compounds of the present invention are stable in vivo, and they either retain in cells after being phosphorylated by mammal thymidine kinase or are incorporated in DNA to reflect the DNA synthesis activity, thus serving for diagnosis of tissue proliferation activity and treatment of proliferative diseases, particularly as radioactive diagnostic imaging agents for tissue proliferation activity diagnosis and as radioactive therapeutic agents for proliferative disease treatment by internal radiotherapy, local radiotherapy and the like.

The invention claimed is:

1. A method for diagnosis of tissue proliferation activity comprising:
administering an effective amount of an agent for diagnosis of tissue proliferation activity to a mammal, said agent comprising, as an active ingredient, a radiolabeled compound as represented by the following formula or a pharmaceutically acceptable salt thereof:

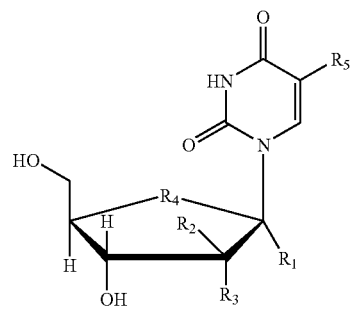

wherein $R_1$ denotes hydrogen, or a linear- or branched-chain alkyl group having 1–8 carbon atoms; $R_2$ denotes hydrogen, hydroxyl, or a halogen substituent; $R_3$ denotes hydrogen or a fluorine substituent, $R_4$ denotes oxygen, sulfur or a methylene substituent, and $R_5$ denotes a radioactive halogen substituent, excluding the case where $R_1$ is hydrogen and $R_4$ is oxygen, and imaging in vivo the distribution of said agent, wherein said diagnosis of tissue proliferation activity is a diagnosis for hyperplasia, tissue regeneration, tissue transplantation or viral infection accompanied by abnormal proliferation.

2. A method according to claim 1, wherein said diagnosis of hyperplasia accompanied by abnormal proliferation is diagnosis of hyperplastic inflammation, benign tumor or malignant tumor.

3. A method according to claim 2, wherein said diagnosis of hyperplastic inflammation is diagnosis concerning activity of chronic rheumatoid arthritis or determination of therapeutic effects thereon.

4. A method according to claim 2, wherein said diagnosis of benign tumor is diagnosis concerning localization, activity or determination of therapeutic effects thereon.

5. A method according to claim 2, wherein said diagnosis of malignant tumor is a diagnosis concerning localization, progress, malignancy or determination of therapeutic effects, wherein said malignant tumor is a primary and metastatic malignant tumor.

6. A nucleoside derivative as represented by the following formula:

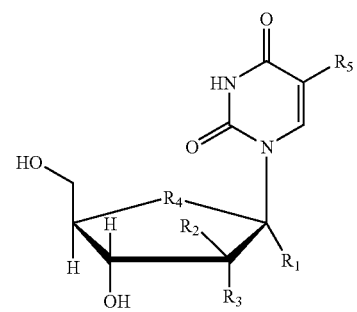

wherein $R_1$ denotes hydrogen or a linear- or branched-chain alkyl groups having 1–8 carbon atoms, $R_2$ denotes hydrogen, hydroxyl or a halogen substituent, $R_3$ denotes hydrogen or a fluorine substituent, $R_4$, denotes oxygen, sulfur or a methylene substituent, and $R_5$ denotes a trialkylstannyl group, excluding the case where $R_1$ is hydrogen and $R_4$ is oxygen.

7. A nucleoside derivative according to claim 6, wherein $R_4$ is sulfur.

8. A nucleoside derivative according to claim 6, wherein $R_1$ is hydrogen or a methyl group, $R_2$ is hydrogen or a halogen-substituent, $R_3$ is hydrogen, and $R_4$ is oxygen or sulfur, excluding the case where $R_1$ is hydrogen and $R_4$ is oxygen.

9. A nucleoside derivative according to claim 6, wherein the trialkylstannyl group in $R_5$ is a trimethylstannyl group, a triethylstannyl group or a tributylstannyl group.

* * * * *